US011325950B2

(12) United States Patent
Pedersen Fischer

(10) Patent No.: US 11,325,950 B2
(45) Date of Patent: May 10, 2022

(54) IMMUNOGENIC FUSION PROTEIN

(71) Applicant: MINERVAX APS, Copenhagen N (DK)

(72) Inventor: Per Bo Pedersen Fischer, Frederiksberg (DK)

(73) Assignee: MINERVAX APS, Copenhagen N (DK)

( * ) Notice: Subject to any disclaimer, the term of this patent is extended or adjusted under 35 U.S.C. 154(b) by 13 days.

(21) Appl. No.: 15/770,153

(22) PCT Filed: Oct. 21, 2016

(86) PCT No.: PCT/EP2016/075356
§ 371 (c)(1),
(2) Date: Apr. 20, 2018

(87) PCT Pub. No.: WO2017/068112
PCT Pub. Date: Apr. 27, 2017

(65) Prior Publication Data
US 2018/0305415 A1   Oct. 25, 2018

(30) Foreign Application Priority Data

Oct. 21, 2015 (SE) .................................... 1551363-3
Dec. 30, 2015 (SE) .................................... 1551725-3

(51) Int. Cl.
C07K 14/315 (2006.01)
A61K 39/09 (2006.01)
A61K 39/00 (2006.01)

(52) U.S. Cl.
CPC .......... *C07K 14/315* (2013.01); *A61K 39/092* (2013.01); *A61K 39/00* (2013.01); *A61K 2039/55505* (2013.01); *A61K 2039/58* (2013.01); *A61K 2039/70* (2013.01); *C07K 2319/00* (2013.01)

(58) Field of Classification Search
None
See application file for complete search history.

(56) References Cited

FOREIGN PATENT DOCUMENTS

| CN | 101821627 A | 9/2010 |
|---|---|---|
| CN | 101855238 A | 10/2010 |
| CN | 102046198 A | 5/2011 |
| EP | 0866133 | 9/2001 |
| WO | 94/10317 | 5/1994 |
| WO | 94/21685 | 9/1994 |
| WO | 2008/127179 | 10/2008 |
| WO | 2009020391 A1 | 2/2009 |
| WO | 2009130618 A2 | 10/2009 |

OTHER PUBLICATIONS

Ellis (Vaccines, W.B. Saunders Company, Chapter 29, 1988, pp. 568-574).*
Boslego et al (Vaccines and Immunotherapy, 1991, Chapter 17).*
Skolnick et al. (Trends in Biotechnology 18: 34-39, 2000).*
Baker et al., "Immunization to Prevent Group B Streptococcal Disease: Victories and Vexations", The Journal of Infectious Diseases, vol. 161, No. 5 (May 1990), pp. 917-921.
Gravekamp et al., "Immunogenicity and Protective Efficacy of the Alpha C Protein of Group B Streptococci Are Inversely Related to the Number of Repeats", Infection and Immunity, Dec. 1997, p. 5216-5221.
Lindahl et al., "Surface Proteins of *Streptococcus agalactiae* and Related Proteins in Other Bacterial Pathogens", Clinical Microbiology Reviews, Jan. 2005, vol. 18, No. 1, p. 102-127.
Maeland et al., "Survey of Immunological Features of the Alpha-Like Proteins of *Streptococcus agalactiae*", Clinical and Vaccine Immunology, Feb. 2015, vol. 22, No. 2, pp. 153-159.
Pritchard et al., "Murine Monoclonal Antibodies to Type Ib Polysaccharide of Group B Streptococci Bind to Human Milk Oligosaccharides", Infection and Immunity, Apr. 1992, vol. 60, No. 4, p. 1598-1602.
Stalhammar-Carlemalm et al., "Nonimmunodominant Regions Are Effective as Building Blocks in a Streptococcal Fusion Protein Vaccine", Cell Host & Microbe 2, 427-434, Dec. 2007.
Auperin et al., "Crystal Structure of the N-terminal Domain of the Group B *Streptococcus* Alpha C Protein", The Journal of Biological Chemistry, vol. 280, No. 18, Issue of May 6, p. 18245-18252, 2005.
Chen et al., "Fusion protein linkers: Property, design and functionality", Advanced Drug Delivery Reviews 65 (2013) 1357-1369.
Frankel et al., "Characterization of diphtheria fusion proteins targeted to the human interleukin-3 receptor", Protein Engineering, vol. 13, No. 8, pp. 575-581, 2000.
Gabrielsen et al., "Molecular characteristics of *Streptococcus agalactiae* strains deficient in alpha-like protein encoding genes", Journal of Medical Microbiology 2017; 66:26-33.

(Continued)

Primary Examiner — Robert A Zeman
(74) Attorney, Agent, or Firm — Adsero IP

(57) ABSTRACT

The present invention relates to an immunogenic fusion protein comprising a first amino acid sequence having at least 80% sequence identity with the amino acid sequence of the N-terminal region of a first group B *Streptococcus* surface protein, which is fused to a second amino acid sequence having at least 80% sequence identity with the amino acid sequence of the N-terminal region of a second group B *Streptococcus* surface protein. Each of the first and the second group B *Streptococcus* surface protein is selected from the group consisting of Rib protein, Alp1 protein, Alp2 protein, Alp3 protein, Alp4 protein and AlpC protein. The immunogenic fusion protein further comprises at least one amino acid sequence having at least 80% sequence identity with the amino acid sequence of the N-terminal region of the group B *streptococcus* surface protein Alp1, Alp2, Alp3 or Alp4. The invention further pertains to an isolated nucleotide sequence encoding the immunogenic fusion protein; a vector; a host cell; an immunogenic product, a vaccine; and a method for preventing or treating a group B *Streptococcus* infection.

6 Claims, 6 Drawing Sheets

Specification includes a Sequence Listing.

(56) References Cited

OTHER PUBLICATIONS

Lachenauer et al., "Mosaicism in the alpha-like protein genes of group B streptococci", PNAS, Aug. 15, 2000, vol. 97, No. 17: 9630-9635.
Maeda et al., Engineering of Functional Chimeric Protein G-*Vargula* Luciferase, Analytical Biochemistry 249, 147-152 (1997).
Pakula et al., "Genetic Analysis of Protein Stability and Function", Annu. Rev. Genet. 1989. 23:289-310.
Russia Office Action for Application No. 2018116601, dated Aug. 21, 2020, along with English translation, 13 pages.
Wang et al., "Immunogenicity of Protein Aggregates—Concerns and Realities," International Journal of Pharmaceutics 431 (2012) 1-11.
Qing-Qing et al., Mining and evaluating the high-effectiveness and broad-spectrum endolysin encoded by prophage harbored in *Streptococcus suis* serotype 7, Microbiology China, Nov. 17, 2014, pp. 1052-1059.
Search Report for CN application 2016800617032 (in Chinese language), dated Jan. 21, 2021, 2 pages.

\* cited by examiner

IMMUNOGENIC FUSION PROTEIN

CROSS-REFERENCE TO RELATED APPLICATION

This application claims priority to and is a 35 U.S.C. § 371 national phase application of PCT/EP2016/075356 (WO2017/068112), filed on Oct. 21, 2016 entitled "IMMUNOGENIC FUSION PROTEIN", which application claims priority to and the benefit of Sweden Patent Application No. 1551363-3, filed Oct. 21, 2015 and Sweden Patent Application No. 1551725-3, filed Dec. 30, 2015; the disclosures of which are incorporated herein by reference in their entirety.

FIELD OF INVENTION

The present invention relates to the fields of microbiology and vaccine technology, and concerns the development of an immunogenic fusion protein capable of conferring immunity to group B *Streptococcus* infections. More particularly, the present invention relates to a novel immunogenic fusion protein which confers immunity to invasive strains of the group B *Streptococcus*. It further pertains to an isolated nucleotide sequence encoding the immunogenic fusion protein; a vector; a host cell; a vaccine; and a method for preventing or treating a group B *Streptococcus* infection.

BACKGROUND OF THE INVENTION

Group B *Streptococcus* (*Streptococcus agalactiae*) (GBS) is the major cause of invasive bacterial infections, including meningitis, in the neonatal period. In the United States alone, there are now about 5000 cases per year of invasive disease caused by this bacterium. These infections have an overall mortality of about 10%, and many of the infants that survive have permanent neurological sequelae. In view of this, a large effort has been made to find methods of prevention and treatment and to analyze the mechanisms by which GBS cause infections.

The GBS can also cause mastitis in cows, a bovine disease that is of considerable economical importance. Development of a vaccine against GBS infections is therefore of interest also in veterinary medicine.

About 20% of all women are vaginal carriers of GBS, and vertical transmission from the maternal genital tract is probably the most common source of infection in neonatal disease caused by this bacterium. However, only about 1% of the infants that are colonized by the GBS at birth are afflicted by serious infection. Other factors than exposure to the bacterium during birth must therefore contribute to the development of neonatal disease.

Group B streptococcal strains are divided into nine serotypes (Ia, Ib, and II-VIII) based on the structure of the polysaccharide capsule (Baker, J Inf Dis 1990. 161: 917). The four "classical" serotypes Ia, Ib, II, and III occur in roughly equal proportions among strains in the normal flora, but type III is the clinically most important serotype, in particular because it causes most cases of meningitis.

Because the capsule is a known virulence factor, it has been studied in considerable detail, in particular in type III strains. Efforts have been made to develop a vaccine, in which the type III polysaccharide capsule would be an essential component.

EP 0 866 133 discloses a vaccine capable of protecting a recipient from infection caused by group B *Streptococcus*. The invention is directed to the use of a combination of a polysaccharide and a fragment of the epsilon protein. It further discloses that epidemiological data suggest that the type-specific capsule plays an important role in the immunity to group B *Streptococcus* infections (se page 7 line 2-3). Additionally, there are a number of different combinations between different proteins and the polysaccharide mentioned within the application but all the claims comprise a polysaccharide which shows the importance of that particular component. However, use of the polysaccharide capsule as a vaccine may give problems due to cross reactions with human tissues (Pritchard et al., Infect Immun 1992. 60: 1598). It would therefore be very valuable if one could develop a vaccine based on proteins rather than on polysaccharides.

The document Gravekamp et al., Infection and Immunity, December 1997, p 5216-5221 discloses the evaluation of the immunogenicity as well as protection of the number of repeats of the alpha (a) C protein as well as the N-terminal part alone. It was found that the immunogenicity decreased with increasing number of repeats (se FIG. 2B). However, it was also found in a protection assay that the antibodies against the N-terminal region were predominantly responsible for the protection compared to antibodies against the N-terminal region (see page 5219 left column, line 6 from the bottom, and page 5220 right column lines 26-29).

WO 9410317 describes the use of the alpha protein, a GBS surface protein, in the development of a conjugate vaccine. A drawback with this protein is that it usually is not expressed by type III strains, which are the cause of many serious GBS infections. Hence, a protective immunity against these strains will not be evoked by an alpha protein vaccine.

WO 9421685 describes the use of the Rib protein, a GBS surface protein, in the development of a vaccine. This protein elicits immunity when administered with alum. However, the Rib protein has the disadvantage that it does not evoke a protective immunity against all GBS strains.

WO 2008127179 describes a fusion protein comprising at least one first N-terminal region fragment of a group B *Streptococcus* surface protein or analogue, homologue, derivative or immunologically related amino acid sequence or fragments thereof, which is fused to at least one second N-terminal region fragment of a group B *Streptococcus* surface protein or analogue, homologue, derivative or immunologically related amino acid sequence or fragments thereof, wherein the first and second at least one N-terminal region fragments of group B *Streptococcus* surface proteins derive from different group B *Streptococcus* strains, and wherein the fusion protein is capable of eliciting protective immunity against group B *Streptococcus*.

The document Lindahl et al, Nonimmunodominant Regions Are Effective As Building Blocks In A Streptococcal Fusion Protein Vaccine, Cell Host & Microbe 2, 427-434, December 2007, discloses a fusion protein comprising N-terminal regions of the group B *Streptococcus* surface proteins Rib and AlpC.

The document Maeland et al, Survey of Immunological Features of the Alpha-Like Proteins of *Streptococcus agalactiae*, Clinical and Vaccine Immunology, February 2015 Volume 22 Number 2, discloses that a two-component vaccine, one immunogenic peptide corresponding to a repeat area stretch of C-alpha or Alp1, either of which cross-reacts strongly (FIG. 2; Table 1), and one peptide corresponding to a repeat area stretch of Alp3 or Rib, either of which also cross-reacts strongly (FIG. 3; Table 1), may provide broad protective activity.

Despite the advances in the progress towards a vaccine suitable for prevention of GBS disease, there is still a need for further methods and vaccines for prevention and treatment of GBS infections. Thus, there remains a need to explore vaccines strategies capable of eliciting protective immunity against a wide range of GBS stains.

Accordingly, it is a primary objective of the present invention to provide an immunogenic fusion protein which can be used in a vaccine capable of eliciting protective immunity against GBS infections.

It is a further objective of the present invention to provide a vaccine that elicits protective immunity against many clinically important GBS strains.

Another objective of the present invention is to provide a vaccine comprising a single, or a few, immunogenic fusion proteins that elicits protective immunity against GBS infections. A single or a few proteins has several advantages over a vaccine composed of numerous proteins, e.g. cost of production and safety.

The means of accomplishing each of the above objectives as well as others will become apparent from the description of the invention which follows hereafter.

SUMMARY OF THE INVENTION

The present invention is based on realization, by the present inventors, that the coverage of the fusion protein disclosed in WO 2008127179 is more limited than previously thought. This is because it was heretofore thought that the important Group B Streptococcus serotype Ia expressed predominantly AlpC surface protein, whereas cross reactivity studies carried out on behalf of the present inventor show that the majority of the Group B Streptococcus serotype Ia bacteria express Alp1 instead of AlpC.

It was furthermore realized that cross-reactivity between different Alp/Rib N-terminal domains cannot be directly predicted based on sequence homologies between the domains. This was realized when the cross-reactivity of rabbit antibodies raised against the previously disclosed Rib-AlpC-NN fusion protein disclosed in WO 2008127179 was tested against N-terminal domains of the Streptococcus Surface proteins Rib, AlpC, Alp1 and Alp2, and against the immunogenic fusion protein according to the first aspect of the present invention as introduced below. The results showed similar reactivities against the Rib-AlpC-NN fusion protein and AlpC N-terminal domains. However, 10-fold lover reactivity was observed against Rib and Alp2 N-terminal domains. Even lower cross-reactivity was observed against Alp1 N-terminal domains, and the immunogenic fusion protein according to the first aspect of the present invention. In addition hereto, mice immunized with the immunogenic fusion protein according to the first aspect of the present invention showed a 2-log reduction in cross-reactivity with the Rib-AlpC-NN fusion protein compared to the titer obtained against the immunogenic fusion protein according to the first aspect of the present invention. Likewise, mice immunized with the Rib-AlpC-NN fusion protein showed a similar reduction in reactivity against the immunogenic fusion protein according to the first aspect of the present invention, and in addition hereto, the maximum amount of binding against the cross-reactive epitopes were also reduced.

Accordingly there was revealed to the present inventors an unexpected need for a further immunogenic fusion protein including Alp1, Alp2, or Alp4, for obtaining protection against Group B Streptococcus infections.

Thus a first aspect of the present invention relates to an immunogenic fusion protein comprising:
  a first amino acid sequence having at least 80% sequence identity with the amino acid sequence of the N-terminal region of a first group B Streptococcus surface protein, which is fused to
  a second amino acid sequence having at least 80% sequence identity with the amino acid sequence of the N-terminal region of a second group B Streptococcus surface protein
wherein each of the first and the second group B Streptococcus surface protein is selected from the group consisting of Rib protein, Alp1 protein, Alp2 protein, Alp3 protein, Alp4 protein and AlpC protein, wherein the immunogenic fusion protein comprises at least one amino acid sequence having at least 80% sequence identity with the amino acid sequence of the N-terminal region of the group B streptococcus surface protein Alp1, Alp2, Alp3 or Alp4, and wherein the immunogenic fusion protein is capable of eliciting protective immunity against group B Streptococcus.

A major advantage of the immunogenic fusion protein of the invention is that it comprises at least one amino acid sequence having at least 80% sequence identity with the amino acid sequence of the N-terminal region of the group B streptococcus surface protein Alp1, Alp2, Alp3 or Alp4, either of which is expressed by many clinically important strains of group B Streptococcus, and most importantly, it will provide protective immunity against these further important strains.

The immunogenic fusion protein has the advantage that it is immunogenic even without adjuvant, however it can also be used with an adjuvant for increased immunogenicity, eliciting protective immunity against strains expressing the surface proteins. Moreover, the immunogenic fusion protein according to the present invention may be used in the vaccine according to the present invention and is expected to be administered with alum or Aluminium hydroxide (AlOH), an adjuvant accepted for use in humans. In contrast, the recently described "universal vaccine" was only reported to work together with Freund's adjuvant, a strongly irritating component that cannot be used in human medicine (Maione, D. et al, Science 2005. 309:148-150).

Another advantage with the present invention is that a vaccine composition according to the invention can be composed of the immunogenic fusion protein according to the first aspect of the present invention combined with a further fusion protein such as the Rib-AlpC-NN fusion protein of WO 2008127179, thus providing an immunogenic product capable of providing full coverage of protection against all clinically relevant Group B Streptococcus strains using only two fusion proteins instead of needing to use 5 or 6, or even more, different capsular proteins.

More specifically, the present invention relates to the immunogenic fusion protein; an immunogenic product; an isolated nucleotide sequence; a vector; a host cell; a vaccine; and a method for preventing or treating a group B Streptococcus infection.

The present invention will be described in more detail below.

DETAILED DESCRIPTION OF THE INVENTION

Figure 1A:
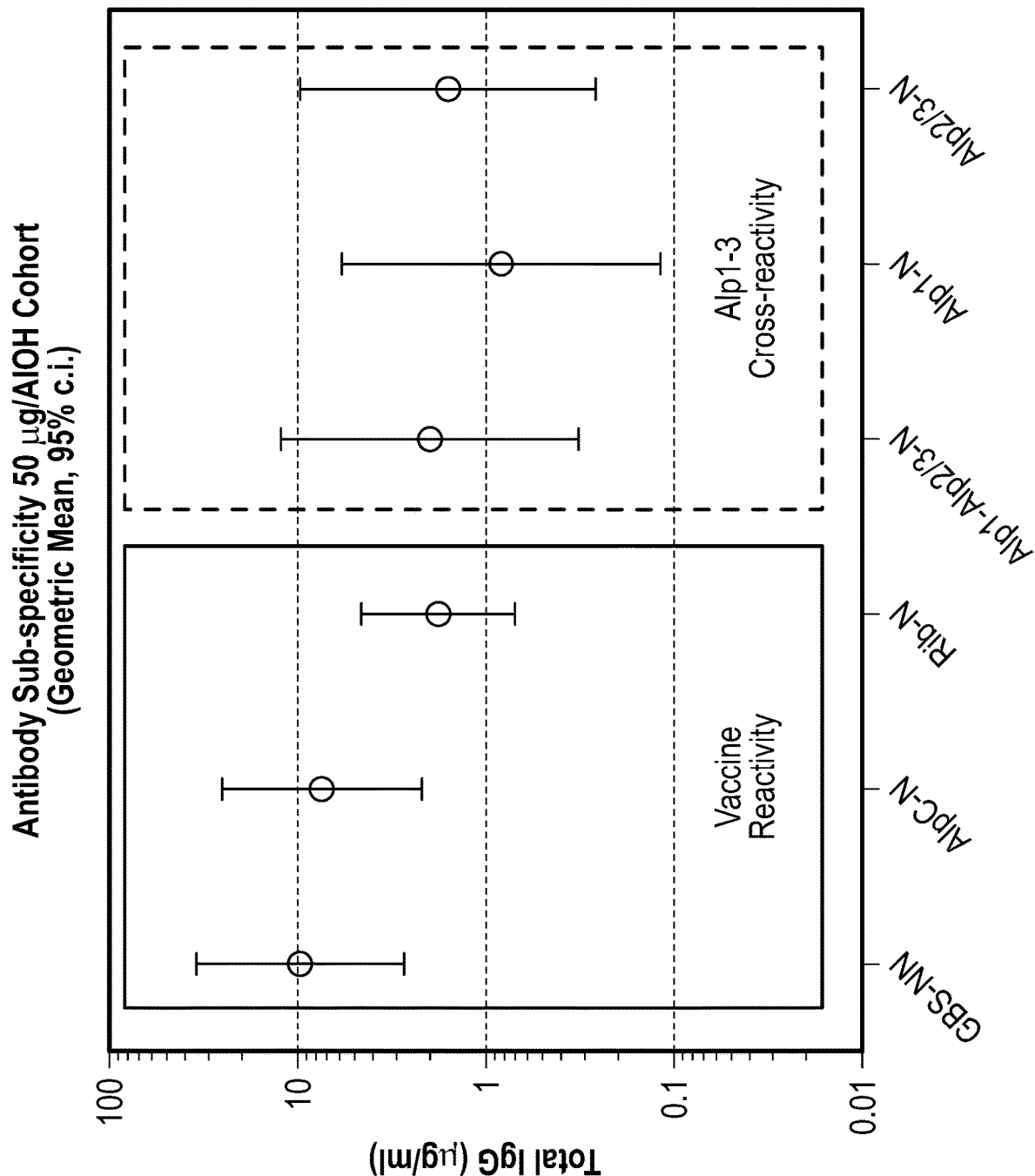
FIG. 1 shows that the Rib-AlpC-NN fusion protein of WO 2008127179 provides higher titers of antibodies against the N-terminal regions of the homotypic N-terminal domains included in the vaccine antigen, than it does against the heterotypic cross-reactive N-terminal domains of Alp1 and Alp2/3. Differences are highlighted by differences in fold-increase in FIG. 1C and the larger spread seen between vaccinated subjects when looking at the absolute numbers in FIG. 1B.

In this specification, unless otherwise specified, "a" or "an" means "one or more".

Throughout the specification, any and all references are specifically incorporated into this patent application by reference.

In a first embodiment of the immunogenic fusion protein according to the first aspect of the present invention the immunogenic fusion protein comprises:
 a first amino acid sequence having at least 80% sequence identity with the amino acid sequence of the N-terminal region of a first group B *Streptococcus* surface protein, which is fused to
 a second amino acid sequence having at least 80% sequence identity with the amino acid sequence of the N-terminal region of a second group B *Streptococcus* surface protein wherein each of the first and the second group B *Streptococcus* surface protein is selected from the group consisting of Rib protein, Alp1 protein, Alp2 protein, Alp3 protein and AlpC protein, wherein the immunogenic fusion protein comprises at least one amino acid sequence having at least 80% sequence identity with the amino acid sequence of the N-terminal region of the group B *streptococcus* surface protein Alp1, Alp2, Alp3 or Alp4, and wherein the immunogenic fusion protein is capable of eliciting protective immunity against group B *Streptococcus*.

The term "immunogenic" is intended to mean having the ability to elicit an immune response. The immunogenic fusion protein of the invention is immunogenic and characterised by its ability to elicit a protective immune response against at least GBS containing the surface proteins of which the N-terminal regions are comprised by the immunogenic fusion protein.

For the purpose of the present invention the term "fusion protein" refers to an assembly of two or more protein regions, or fragments thereof, comprising for example an N-terminal region of a group B *Streptococcus* Alp1 protein and an N-terminal region of a group B *Streptococcus* Alp2 protein. For example there might be one N-terminal region of the Alp1- and one N-terminal region of the Alp2, or 2, 3, 4 or 5 N-terminal region fragments of the Alp1- and the Alp2-proteins, wherein the numbers of N-terminal regions from the two proteins need not be equal.

The combination of polypeptides to provide a fusion protein can be accomplished by several means, e.g.: chemically by coupling, conjugation or cross-linking, either directly or through an intermediate structure; physically by coupling through capture in or on a macromolecular structure; or by molecular biological fusion, through the combination of recombinant nucleic acid molecules which comprise fragments of nucleic acid capable of encoding each of the two, such that a single continuous expression product is finally produced.

For the purpose of the present invention the term "protein" refers to a molecular chain of amino acids. A protein is not of a specific length and can, if required, be modified in vivo or in vitro, by, for example, glycosylation, amidation, carboxylation or phosphorylation. Inter alia, peptides, oligopeptides and polypeptides are included within the definition. The protein or peptide can be of natural or synthetic origin. In this context a fusion protein is intended to mean two or more polypeptides covalently linked to each other either directly or indirectly by several means such as those mentioned above. The term "fused" means to create a fusion protein as mentioned above.

The term "N-terminal region" in relation to the present invention refers to an N-terminus region (N) of a protein. Examples of amino acid sequences of the N-terminal regions of the group B *Streptococcus* surface proteins are given in SEQ IDs NO: 2, 4, 8, 10 and 14.

In particular, examples of N-terminal regions of group B *Streptococcus* proteins include the N-terminal region of the group B *Streptococcus* Rib, Alp1, Alp2, Alp3, Alp4 and AlpC protein, including peptides encoding native amino acid sequences of N-terminal regions of natural Rib, Alp1, Alp2, Alp3, Alp4 and AlpC protein, or may be functional derivatives of native sequences of these regions wherein these functional derivatives retain their ability to elicit protective immunity against the group B *Streptococcus*. The term functional derivatives is intended to include parts of sequences and fragments of the N-terminal regions; it is also intended to include variants of the natural proteins (such as proteins having changes in amino acid sequence but which retain the ability to elicit an immunogenic, virulence or antigenic property as exhibited by the natural molecule), for example, with altered flanking sequence.

Group B streptococcal strains, also referred herein as GBS, are well known and may be isolated from the blood of infected human beings. GBS is the most common cause of neonatal sepsis in the United States and is responsible for about 5000 cases per year.

The denotation "Group B streptococcal" derives from the fact that Streptococci have been divided into immunological groups based upon the presence of specific carbohydrate antigens on their cell surfaces. At present, groups A through O are recognized (Davis, B. D. et al., In: Microbiology, 3rd. Edition, page 609, (Harper & Row, 1980).

Percent homology can be determined, for example, by comparing sequence information using the GAP computer program, version 6.0, available from the University of Wisconsin Genetics Computer Group (UWGCG). The GAP program utilizes the alignment method of Needleman and Wunsch (J Mol Biol 1970 48:443), as revised by Smith and Waterman (Adv Appl Math 1981 2:482). Briefly, the GAP program defines similarity as the number of aligned symbols (i.e., nucleotides or amino acids) which are similar, divided by the total number of symbols in the shorter of the two sequences. The preferred default parameters for the GAP program include: (1) a unitary comparison matrix (containing a value of 1 for identities and 0 for non-identities) and the weighted comparison matrix of Gribskov and Burgess (Nucl Acids Res 1986 14:6745), as described by Schwartz and Dayhoff, eds. (Atlas of Protein Sequence and Structure, National Biomedical Research Foundation, Washington, D.C. 1979, pp. 353-358); (2) a penalty of 3.0 for each gap and an additional 0.10 penalty for each symbol in each gap; and (3) no penalty for end gaps.

The group B *Streptococcus* Rib protein, also referred to in this specification as Rib and Rib protein, is a surface protein known in the art, and for example described in WO 9421685. The denotation "Rib" refers to: Resistance to proteases, immunity, and group B. The Rib protein was first isolated from a group B streptococcal strain of serotype III as a distinct 95 kDa protein. Protein Rib is expressed by almost all group B streptococcal strains of the clinically important serotype III, which cause most cases of meningitis, and by some strains of other serotypes such as II. Moreover, Rib is expressed by all strains of a hypervirulent clone of type III. A method has been devised to purify protein Rib and it has been demonstrated that antibodies to this protein protect against lethal infection with strains expressing protein Rib (for further details, such as DNA and protein sequences see WO 9421685). The nucleic acid sequence and the amino acid sequence for the N-terminal region of Rib are given in SEQ ID Nos: 1 and 2.

The Alp1 protein is also known as epsilon protein and is a group B streptococcal alpha-protein-like protein (Creti et al. *Clin Microbiol.* 2004.42:1326-9).

The nucleic acid sequence and the amino acid sequence for the N-terminal region of Alp1 are given in SEQ ID Nos: 7 and 8. The amino acid sequence is (SEQ ID No 8):

MAEVISGSAATLNSALVKNVSGGKAYIDIYDVKNGKIDPLNLIVLTPSNY

SANYYIKQGGRIFTSVNQLQTPGTATITYNILDENGNPYTKSDGQIDIVS

LVTTVYDTTELRNNINKVIENANDPKWSDDSRKDVLSKIEVIKNDIDNNP

KTQSDIDNKIVEVNELEKLLVLP

The Alp2 protein is another alpha-protein-like-protein first identified in a serotype V strain (Lachenauer, C. S., R. Creti, J. L. Michel, and L. C. Madoff. 2000. Mosa-icism in the alpha-like protein genes of group B streptococci. Proc. Natl. Acad. Sci. USA 97:9630-9635.). Like the other members of the family, the Alp2 protein has an N-terminal domain and several repeated domains towards the C-terminus. Subsequently that protein has been found also in other GBS isolates such as serotypes Ia and III (Lindahl et al. Surface Proteins of *Streptococcus agalactiae* and Related Proteins in Other Bacterial Pathogens, CLINICAL MICROBIOLOGY REVIEWS, January 2005, p. 102-127). The nucleic acid sequence and the amino acid sequence for the N-terminal region of Alp2 are given in SEQ ID Nos: 9 and 10.

The Alp3 protein is yet another alpha-protein-like-protein, also know as R28. It is very similar to the R28 protein also found in S. pyrogenes. (Lachenauer, C. S., R. Creti, J. L. Michel, and L. C. Madoff. 2000. Mosa-icism in the alpha-like protein genes of group B streptococci. Proc. Natl. Acad. Sci. USA 97:9630-9635 and Lindahl et al. Surface Proteins of *Streptococcus agalactiae* and Related Proteins in Other Bacterial Pathogens, CLINICAL MICROBIOLOGY REVIEWS, January 2005, p. 102-127). The structure is more complex than the other Alpha-protein-like-proteins, but it retains an N-terminal domain which is identical to that of Alp2, and C-terminal repeat regions very similar to Rib. The nucleic acid sequence and the amino acid sequence for the N-terminal region of Alp3 are the same as for Alp2 and are given in SEQ ID Nos: 9 and 10.

The Alp4 protein is an alpha-protein-like-protein so far only identified in the Prague 25/60 strain (Fanrong Kong, Sonia Gowan, Diana Martin, Gregory James, and Gwendolyn L. Gilbert. Molecular Profiles of Group B Streptococcal Surface Protein Antigen Genes: Relationship to Molecular Serotypes. JOURNAL OF CLINICAL MICROBIOLOGY, February 2002, p. 620-626). It is a novel member of the Alpha-protein-like family with a structure similar to that of the other members, with a distinct N-terminal domain, and repeat regions towards the C-terminus.

The nucleic acid sequence and the amino acid sequence for the N-terminal region of Alp4 are given in SEQ ID Nos 13 and 14.

The group B *Streptococcus* AlpC protein, also known as alpha protein, is a group B *Streptococcus* surface protein known in the art. WO 9410317 describes a conjugate vaccine composition comprising the alpha protein. The native group B *Streptococcus* AlpC precursor protein as described in WO 9410317 has a molecular weight of 108 kDa. Cleavage of the putative signal sequence of 41 amino acids yields a mature protein of 104 kDa. (Note, however, that the signal sequence was subsequently shown to have a length of 56 amino acid residues: Stålhammar-Carlemalm et al., J Exp Med 177, 1593; 1993). The 20 kDa N-terminal region of the AlpC antigen shows no homology to previously described protein sequences and is followed by a series of nine tandem repeating units that make up 74% of the mature protein. Each repeating unit (denoted herein as "R") is identical and consists of 82 amino acids with a molecular mass of about 8500 Daltons, which is encoded by 246 nucleotides. The C-terminal region of the AlpC antigen contains a cell wall anchor domain motif present in a number of Gram-positive surface proteins.

The nucleic acid sequence and the amino acid sequence for the N-terminal region of AlpC are given in SEQ ID Nos: 3 and 4.

Each of the Rib, Alp1, and AlpC proteins of GBS includes a unique N-terminal region (N) and a long repeat (R) region. The proteins expressed by the GBS strains BM110 and A909 have 12 and 9 repeats, respectively. The wall anchoring regions are located at the C-terminal ends.

The N-terminal regions of Alp2 and Alp3 are identical.

The tandem repeats in Rib and alpha are identical within each protein, but not between the proteins, and vary in number between isolates. Except for this variation, the sequences of Rib and alpha are stable among strains. The two proteins show little or no antigenic cross-reactivity.

The term "protective immunity" in relation to the present invention refers to the ability of serum antibodies and/or cytotoxic T cell response induced during immunization to protect (partially or totally) against disease caused by an infectious agent, such as a group B *Streptococcus*. That is, a vertebrate immunized by the vaccines of the invention will experience limited growth and spread of group B *Streptococcus*. To determine whether protective immunity is induced by a fusion protein or vaccine, techniques well known for a person skilled in the art can be used. For example, to determine whether immunization with a fusion protein or vaccine of the invention induces protective immunity against group B *Streptococcus* infection, immunized test animals can be challenged with group B *Streptococcus* and growth and spread of the group B *Streptococcus* is measured. For example to determine whether protective immunity is induced, methods in accordance with the methods described in the examples below can be used.

In one embodiment of the immunogenic fusion protein according to the first aspect of the present invention the first amino acid sequence may have at least 90 such as 95, 96, 97, 98 or 99% sequence identity with the amino acid sequence of the N-terminal region of the first group B *Streptococcus* surface protein, and the second amino acid sequence may have at least 90, such as at least 95, 96, 97, 98 or 99% sequence identity with the amino acid sequence of the N-terminal region of the second group B *Streptococcus* surface protein.

The immunogenic fusion protein comprises at least one amino acid sequence having at least 80%, such as at least 90 such as 95, 96, 97, 98, or 99% sequence identity with the amino acid sequence of the N-terminal region of the group B *streptococcus* surface protein Alp1, Alp2, Alp3 or Alp4.

In one preferred embodiment of the immunogenic fusion protein according to the first aspect of the present invention the immunogenic fusion protein comprises at least one amino acid sequence having at least 80%, such as at least 90 such as 95, 96, 97, 98, or 99% sequence identity with the amino acid sequence of the N-terminal region of the group B *streptococcus* surface protein Alp1, Alp2 or Alp3.

In a more preferred embodiment of the immunogenic fusion protein according to the first aspect of the present invention the immunogenic fusion protein comprises at least one amino acid sequence having at least 80%, such as at least 90 such as 95, 96, 97, 98, or 99% sequence identity with the amino acid sequence of the N-terminal region of the group B *streptococcus* surface protein Alp1.

In a further embodiment of the immunogenic fusion protein according to the first aspect of the present invention the immunogenic fusion protein further comprises
   a third amino acid sequence having at least 80% sequence identity with the amino acid sequence of the N-terminal region of a third group B *Streptococcus* surface protein, which is fused to one of the first and second amino acid sequences, the third group B *Streptococcus* surface protein being selected from the group consisting of Rib protein, Alp1 protein, Alp2 protein, Alp3 protein, Alp4 protein and AlpC protein, This is advantageous as it provides for an immunogenic fusion protein capable of eliciting protective immunity against a larger number of group B *Streptococcus* strains.

In one embodiment of the immunogenic fusion protein according to the first aspect of the present invention the third amino acid sequence has at least 90 such as at least 95, 96, 97, 98 or 99% sequence identity with the amino acid sequence of the N-terminal region of the third group B *Streptococcus* surface protein.

In a further embodiment of the immunogenic fusion protein according to the first aspect of the present invention the immunogenic fusion protein further comprises a fourth amino acid sequence having at least 80% sequence identity with the amino acid sequence of the N-terminal region of a fourth group B *Streptococcus* surface protein, which is fused to one of the first and third amino acid sequences, the fourth group B *Streptococcus* surface protein being selected from the group consisting of Rib protein, Alp1 protein, Alp2 protein, Alp3 protein, Alp4 protein and AlpC protein.

This is advantageous as it provides for an immunogenic fusion protein capable of eliciting protective immunity against a larger number of group B *Streptococcus* strains.

In one embodiment of the immunogenic fusion protein according to the first aspect of the present invention the fourth amino acid sequence has at least 90 such as at least 95, 96, 97, 98 or 99% sequence identity with the amino acid sequence of the N-terminal region of the fourth group B *Streptococcus* surface protein.

It should be emphasized that the first, second, third and fourth amino acid sequences may be arranged in any order in the immunogenic fusion protein. That being said the amino acid sequences are preferably arranged from first to fourth.

In one embodiment of the immunogenic fusion protein according to the first aspect of the present invention the immunogenic fusion protein consists of the first and the second amino acids sequences, the first, second and third amino acid sequences, or alternatively the first, second, third and fourth amino acid sequences.

In a further embodiment of the immunogenic fusion protein according to the first aspect of the present invention the first and second group B *Streptococcus* surface proteins, or optionally the first, second and third group B *Streptococcus* surface proteins, or optionally the first, second, third and fourth group B *Streptococcus* surface proteins, are derived from different group B *Streptococcus* strains.

This will imply slight variability in the sequence of the N-terminal region fragments but would not alter the biological properties and their functional ability to elicit protective immunity. This is advantageous as it increases the number of group B *Streptococcus* strains which the immunogenic fusion protein according to the first aspect of the present invention provides protection against.

In a further embodiment of the immunogenic fusion protein according to the first aspect of the present invention the first and second group B *Streptococcus* surface proteins, or optionally the first, second and third group B *Streptococcus* surface proteins, or optionally the first, second, third and fourth group B *Streptococcus* surface proteins, are different.

This is advantageous as it increases the number of group B *Streptococcus* strains which the immunogenic fusion protein according to the first aspect of the present invention provides protection against.

In a further embodiment of the immunogenic fusion protein according to the first aspect of the present invention one of the first and second group B *Streptococcus* surface proteins is Alp1 protein and the other is Alp2 protein, or vice versa.

This is advantageous as it is expected that the fusion of the N-terminals of Alp1 and Alp2 will provide benefits in protecting against group B *Streptococcus*.

In a further embodiment of the immunogenic fusion protein according to the first aspect of the present invention the first amino acid sequence has at least 80%, such as at least 85%, such as at least 90%, such as 95, 96, 97, 98 or 99% sequence identity with the amino acid sequence SEQ ID NO:8, and
   the second amino acid sequence has at least 80%, such as at least 85%, such as at least 90%, such as 95, 96, 97, 98 or 99% sequence identity with the amino acid sequence SEQ ID NO:10.

The term "sequence identity" indicates a quantitative measure of the degree of homology between two amino acid sequences of equal length or between two nucleotide sequences of equal length. If the two sequences to be compared are not of equal length, they must be aligned to best possible fit. Sequence identity can, for example, be calculated by the BLAST program e.g. the BLASTP program or the BLASTN program (Pearson W. R and D. J. Lipman (1988) PNAS USA 85:2444-2448) (www.ncbl.nlm.nlh.gov/BLAST).

In a further embodiment of the immunogenic fusion protein according to the first aspect of the present invention the immunogenic fusion protein comprises an amino acid sequence having at least 80%, such as at least 85%, such as at least 90%, such as 95, 96, 97, 98 or 99% sequence identity with the amino acid sequence shown in SEQ ID NO:12.

SEQ ID NO: 12 shows the amino acid sequence of an immunogenic fusion protein comprising the N-terminal of Alp1 fused to the N-terminal of Alp2. The amino acid sequence (SEQ ID NO: 12) is:

MAEVISGSAATLNSALVKNVSGGKAYIDIYDVKNGKIDPLNLIVLTPSNY

SANYYIKQGGRIFTSVNQLQTPGTATITYNILDENGNPYTKSDGQIDIVS

LVTTVYDTTELRNNINKVIENANDPKWSDDSRKDVLSKIEVIKNDIDNNP

KTQSDIDNKIVEVNELEKLLVLPEFSTIPGSAATLNTSITKNIQNGNAYI

DLYDVKNGLIDPQNLIVLNPSSYSANYYIKQGAKYYSNPSEITTTGSATI

TFNILDETGNPHKKADGQIDIVSVNLTIYDSTALRNRIDEVINNANDPKW

SDGSRDEVLTGLEKIKKDIDNNPKTQIDIDNKINEVNEIEKLLVVSL

In a further embodiment of the immunogenic fusion protein according to the first aspect of the present invention the immunogenic fusion protein is modified by glycosylation, amidation, carboxylation or phosphorylation, or by being conjugated to a capsular polysaccharide or an RSV antigen as described with regard to the third aspect of the present invention further below.

This is advantageous as such polypeptides may have enhanced immunogenicity. Such polypeptides may result when the native forms of the polypeptides or fragments thereof are modified or subjected to treatments to enhance their immunogenic character in the intended recipient. Numerous techniques are available and well known to those of skill in the art which may be used, without undue experimentation, to substantially increase the immunogenicity of the polypeptides herein disclosed. For example, the polypeptides may be modified by coupling to dinitrophenol groups or arsanilic acid, or by denaturation with heat and/or SDS. Particularly if the polypeptides are small polypeptides synthesized chemically, it may be desirable to couple them to an immunogenic carrier. The coupling of course, must not interfere with the ability of either the polypeptide or the carrier to function appropriately. For a review of some general considerations in coupling strategies, see Antibodies, A Laboratory Manual, Cold Spring Harbor Laboratory, ed. E. Harlow and D. Lane (1988). Useful immunogenic carriers are well known in the art. Examples of such carriers are keyhole limpet hemocyanin (KLH); albumins such as bovine serum albumin (BSA) and ovalbumin, PPD (purified protein derivative of tuberculin); red blood cells; tetanus toxoid; cholera toxoid; agarose beads; activated carbon; or bentonite.

A second aspect of the present invention concerns an immunogenic product comprising the immunogenic fusion protein according to the first aspect of the present invention and further comprising a second immunogenic protein comprising at least two amino acid sequences, wherein the two amino acid sequences consists of a first amino acid sequence having at least 80%, such as at least 85%, such as at least 90%, such as 95, 96, 97, 98 or 99% sequence identity with an amino acid sequence as shown in SEQ ID NO:2, fused to a second amino acid sequence having at least 80%, such as at least 85%, such as at least 90%, such as 95, 96, 97, 98 or 99% sequence identity with an amino acid sequence as shown in SEQ ID NO:4, wherein the second immunogenic fusion protein is capable of eliciting protective immunity against group B *Streptococcus*.

The second immunogenic fusion protein may have the amino acid sequence shown in SEQ ID NO: 6. A corresponding DNA sequence is shown in SEQ ID NO: 5. This is advantageous as it provides an immunogenic product capable of providing full coverage of protection against all clinically relevant Group B *Streptococcus* strains using only two fusion proteins instead of needing to use 5 or 6, or even more, different capsular proteins.

Preferably the immunogenic product according to the second aspect of the present invention comprises the immunogenic fusion protein according to the first aspect of the present invention wherein one of the first and second group B *Streptococcus* surface proteins (in the immunogenic fusion protein) is Alp1 protein and the other is Alp2 protein. More preferably the first amino acid sequence (in the immunogenic fusion protein) has at least 80%, such as at least 85%, such as at least 90%, such as 95, 96, 97, 98 or 99% sequence identity with the amino acid sequence SEQ ID NO:8, and the second amino acid sequence (in the immunogenic fusion protein) has at least 80%, such as at least 85%, such as at least 90%, such as 95, 96, 97, 98 or 99% sequence identity with the amino acid sequence SEQ ID NO:10. Even more preferably the immunogenic fusion protein comprises an amino acid sequence having at least 80%, such as at least 85%, such as at least 90%, such as 95, 96, 97, 98 or 99% sequence identity with the amino acid sequence shown in SEQ ID NO:12.

Thus in one preferred embodiment of the immunogenic product according to the second aspect of the present invention the immunogenic fusion protein comprises the amino acid sequence shown in SEQ ID NO:12, and the second immunogenic fusion protein comprises the amino acid sequence shown in SEQ ID NO: 6.

Further, in one embodiment of the immunogenic product according to the second aspect of the present invention the immunogenic fusion protein consists of the amino acid sequence shown in SEQ ID NO:12 and the second immunogenic fusion protein consists of the amino acid sequence shown in SEQ ID NO: 6. Preferably there are no other proteins or amino acids sequences, different from the amino acid sequences in SEQ ID NO:6 and 12, in the immunogenic product.

Figure 1B:
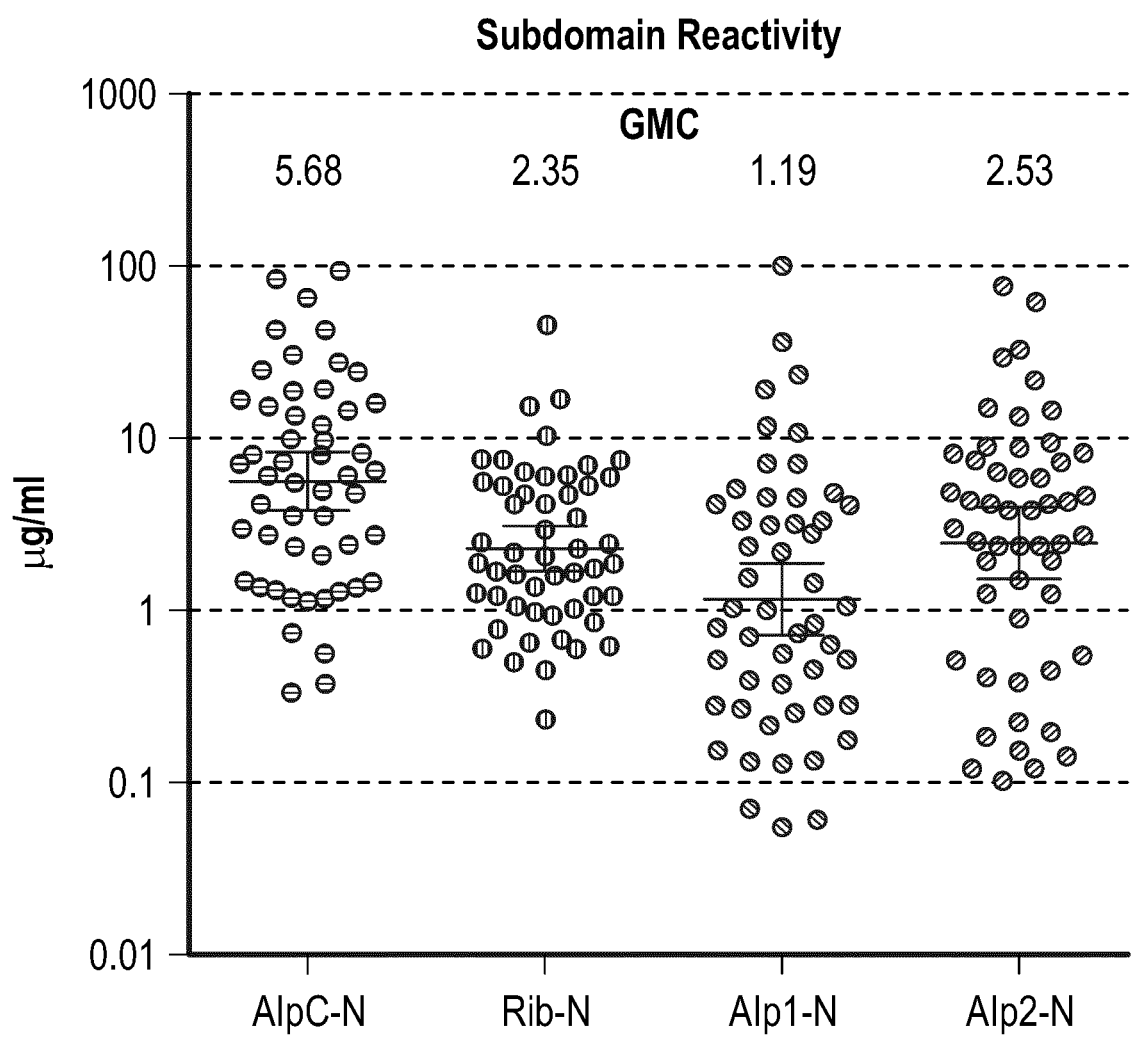
Figure 1C:
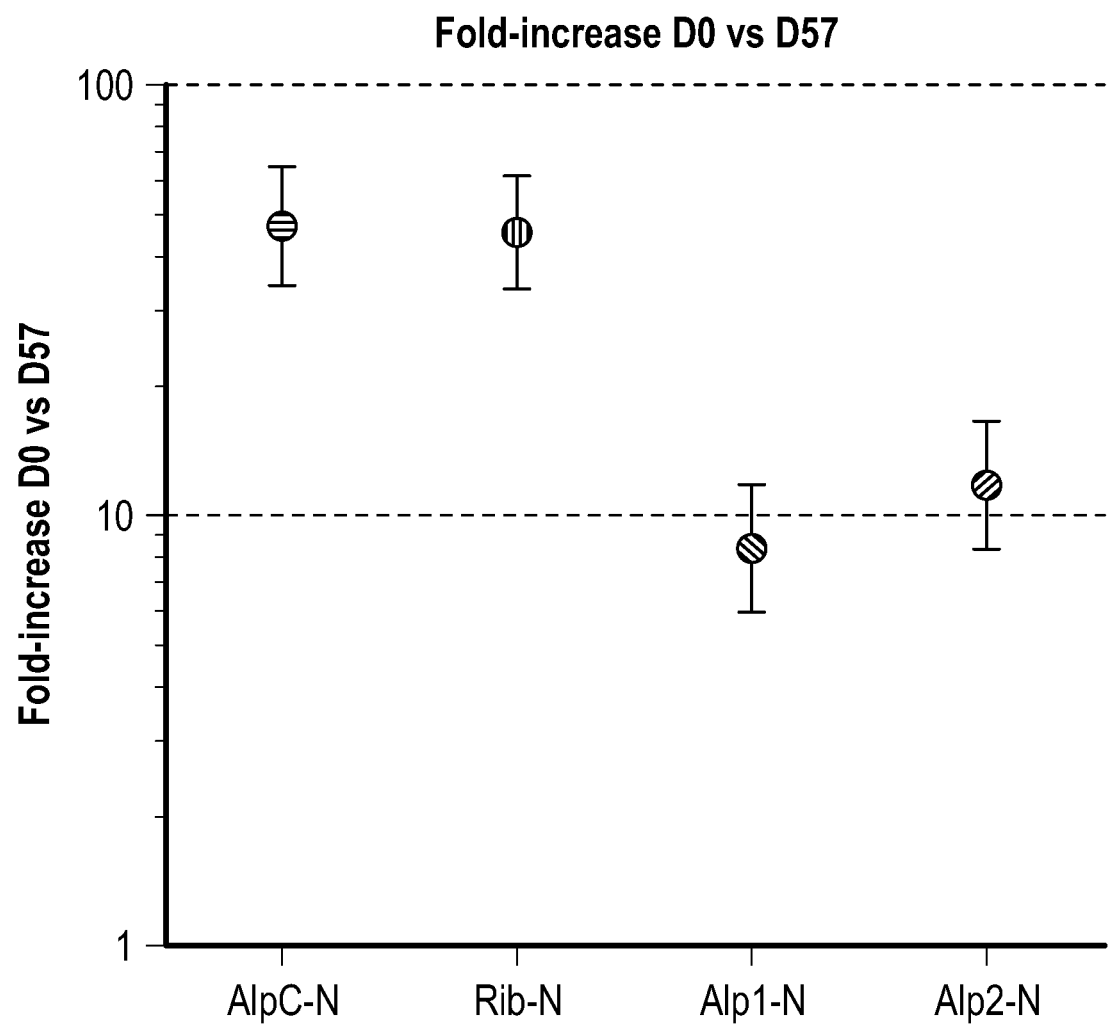
Figures 2A, 2B, 2C:
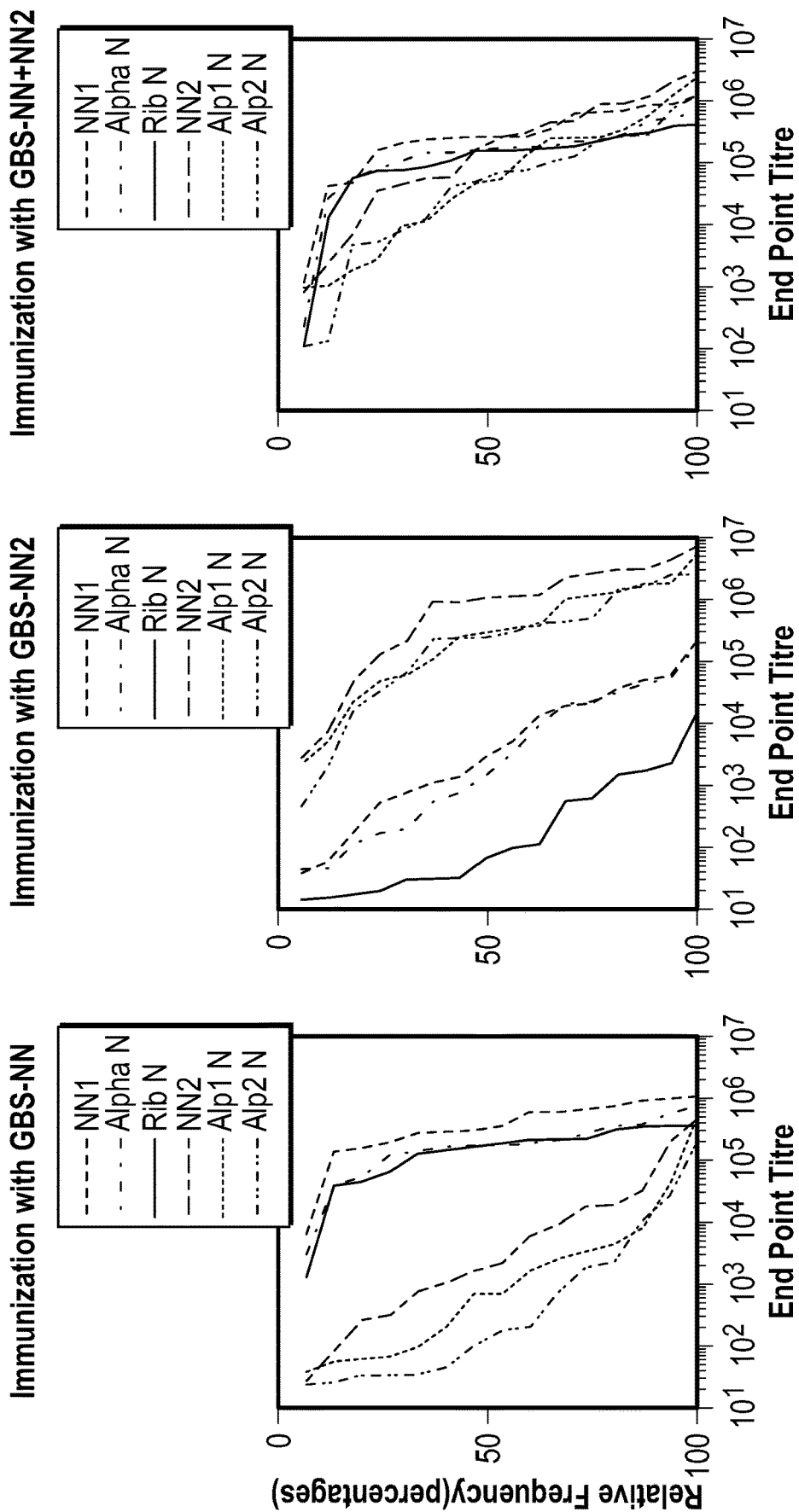
FIG. 2 shows that a vaccine composition according to the present invention composed of an immunogenic fusion protein according to the first aspect of the present invention combined with the Rib-AlpC-NN fusion protein of WO 2008127179 provides maximal coverage against all N-terminals, i.e. adding the remaining N-terminal domains to the vaccine composition enhances the response to these domains over and above what is provided in terms of cross-reactivity provided by the Rib-AlpC-NN fusion protein alone.

FIG. 1A shows that the Rib-AlpC-NN fusion protein of WO 2008127179 provides higher titers of antibodies against the N-terminal regions of the homotypic N-terminal domains included in the vaccine antigen, than it does against the heterotypic cross-reactive N-terminal domains of Alp1 and Alp2/3. Differences are highlighted by differences in fold-increase in FIG. 1C and the larger spread seen between vaccinated subjects when looking at the absolute numbers in FIG. 1B. The effect of the immunogenic product according to the second aspect of the present invention is further shown in FIG. 2A-C. Thus FIG. 2A shows that immunization with a RibN-AlpCN fusion protein of WO 2008127179 (referred to as GBS-NN) provides equal titers against the N-terminal regions or Rib and AlpC, but less cross-reactive titers. On the other hand immunization with an Alp1N-Alp2/3N fusion protein according to the first aspect of the present invention (referred to as GBS-NN2) provides equal titers against the N-terminal regions of Alp1 and Alp2/3, however also here with less cross-reactive titers, as seen in FIG. 2B. When the two fusion proteins are combined in the immunogenic product according to the second aspect of the present invention (referred to as GBS-NN+NN2) as in FIG. 2C, the coverage (titers) is increased for all N-terminal regions of the Rib, AlpC, Alp1, Alp2/3. Accordingly, a very broad protection against GBS is achieved by the immunogenic product according to the second aspect of the present invention.

Figure 3:
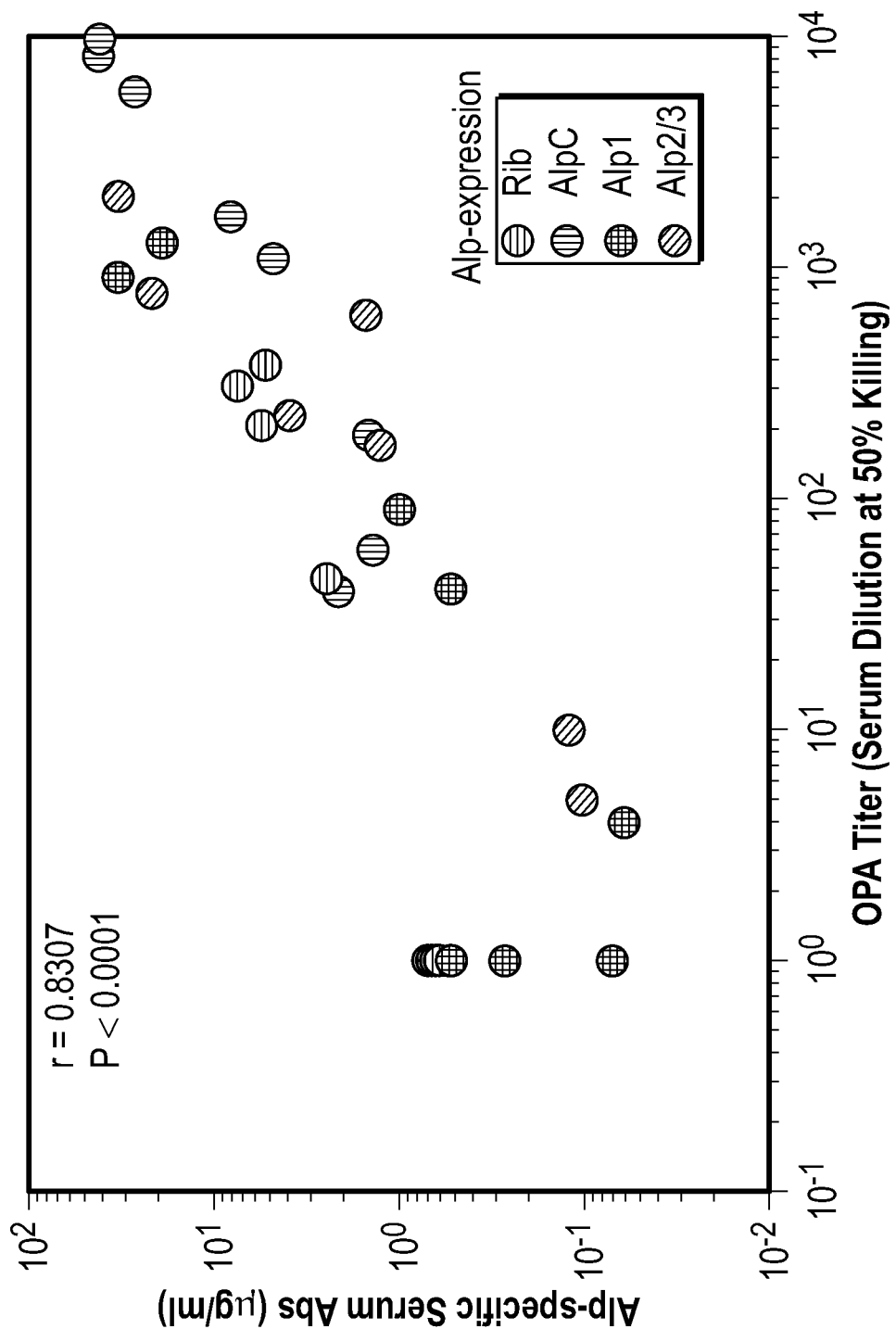
FIG. 3 shows that there is a linear correlation between IgG levels for the immunogenic fusion protein of WO 2008127179 and OPA titers against both vaccine- and cross-reactive Alp strains, meaning that those subjects obtaining high levels of antibodies also against the remaining N-terminal domains these will also be functionally active. Such high levels are however obtained in fewer subjects when immunized with the Rib-AlpC-NN fusion protein alone, hence the inclusion of additional N-terminal domains in the vaccine composition.

Further, FIG. 3 shows that that there is a linear correlation between IgG levels for the RibN-AlpCN immunogenic fusion protein of WO 2008127179 and OPA titers against both vaccine- and cross-reactive Alp strains. Thus FIG. 3 shows that antibodies generated against the RibN-AlpCN immunogenic fusion protein, specific for the N-terminals or Rib and AlpC found in the fusion protein as well as specific for the other N-terminal regions, i.e. the N-terminal regions for Alp1 and Alp2/3 (for Alp1N and alp2/3N by cross-reactivity) are functionally active and can kill GBS bacteria with opsono-phagocytosis. This means that those subjects obtaining high levels of antibodies also against the remaining N-terminal domains these will also be functionally active. Such high levels are however obtained in fewer subjects when immunized with the Rib-AlpC-NN fusion protein alone, hence the inclusion of additional N-terminal domains, i.e. the immunogenic fusion protein according to the first aspect of the present invention, in the immunogenic product and/or the vaccine.

A third aspect of the present invention concerns a vaccine comprising a pharmaceutically acceptable vehicle, optionally an adjuvant, and a pharmaceutically effective amount of an immunogenic fusion protein according to the first aspect of the present invention or an immunogenic product according to the second aspect of the present invention wherein the vaccine is capable of eliciting protective immunity against group B Streptococcus.

The term "pharmaceutical acceptable vehicle" is intended to mean any suitable acceptable excipient, adjuvants, carrier, diluent commonly used in pharmaceutical formulations.

The vaccine may be a vaccine composition.

The vaccine may, in addition to the fusion protein, comprise other pharmacologically acceptable ingredients such as salts, buffers, immunoactive components, adjuvants (AlOH), wetting agents, emulsifying and suspending agents, or sweetening, flavouring, perfuming agents, or other substances which are desirable for improving the efficacy of the composition. A composition is said to be "pharmacologically acceptable" if its administration can be tolerated by a recipient individual.

In a preferred embodiment of the vaccine according to the third aspect of the present invention the vaccine comprises a pharmaceutically effective amount of the immunogenic product according to the second aspect of the present invention.

This is advantageous as the immunogenic product provides broad protection against GBS.

A multivalent vaccine may also be prepared by combining the immunogenic fusion protein or the immunogenic product with other components, including other fusion proteins as described above, including but not limited to diphtheria toxoid or tetanus toxoid, or polysaccharides, using techniques known in the art. The vaccine may further comprise further antigens such as RSV antigens or E. coli antigens.

Methods for the preparation and formulation of vaccines and vaccine compositions are well known to those skilled in the art. The choice of ingredients will for instance vary depending on the administration route of the composition. For example compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water.

In a further embodiment of the third aspect of the present invention the vaccine may comprise an additional immunoactive component. The additional immunoactive component may be an antigen, an immune enhancing substance, and/or a vaccine; either of these may comprise an adjuvant.

Adjuvants are substances that can be used to specifically augment a specific immune response. Normally, the adjuvant and the composition are mixed prior to presentation to the immune system, or presented separately, but into the same site of the animal or human being immunized. Adjuvants can be loosely divided into several groups based upon their composition. These groups include oil adjuvants (for example, Freund's complete and incomplete), mineral salts for example, AlK $(SO_4)_2$, AlNa $(SO_4)_2$, AlNH$_4$ $(SO_4)$, AlOH, silica, kaolin, and carbon), polynucleotides (for example, poly IC and poly AU acids), and certain natural substances (for example, wax D from *Mycobacterium tuberculosis*, as well as substances found in *Corynebacterium parvum*, or *Bordetella pertussis*, and members of the genus *Brucella*. Among those substances particularly useful as adjuvants are saponins such as, for example, Quil A. Examples of materials suitable for use in vaccine compositions are provided in Remington's Pharmaceutical Sciences (Osol, A, Ed, Mack Publishing Co, Easton, Pa., pp. 1324-1341 (1980).

The impact of two different adjuvants on the immune response of the previously described fusion protein of WO 2008127179 has been tested in mice. The mice were immunized once at day 0 without adjuvant, or with Alhydrogel (aluminium hydroxide) or PolyIC as an adjuvant. At week 15, significantly higher titers were seen in mice immunized in the presence of Alhydrogel (approx. $5 \times 10^3$), compared both to without adjuvant (approx. $2 \times 10^1$) and with PolyIC (approx. $10^2$).

Challenging the mice at week 15 with protein without adjuvants, and measuring at antibody titers at week 16, had relatively little effect on the group originally receiving protein without adjuvant (A), a 1-log increase on the PolyIC group (C), but relatively little effect on the already high Alhydrogel group (B). Even though the titers in the PolyIC group did increase it did not reach the level of the Alhydrogel group.

Thus it is expected that Alhydrogel will be an especially effective adjuvant for the immunogenic fusion protein according to the first aspect of the present invention and therefore especially useful in the vaccine according to the third aspect of the present invention.

Figure 4:
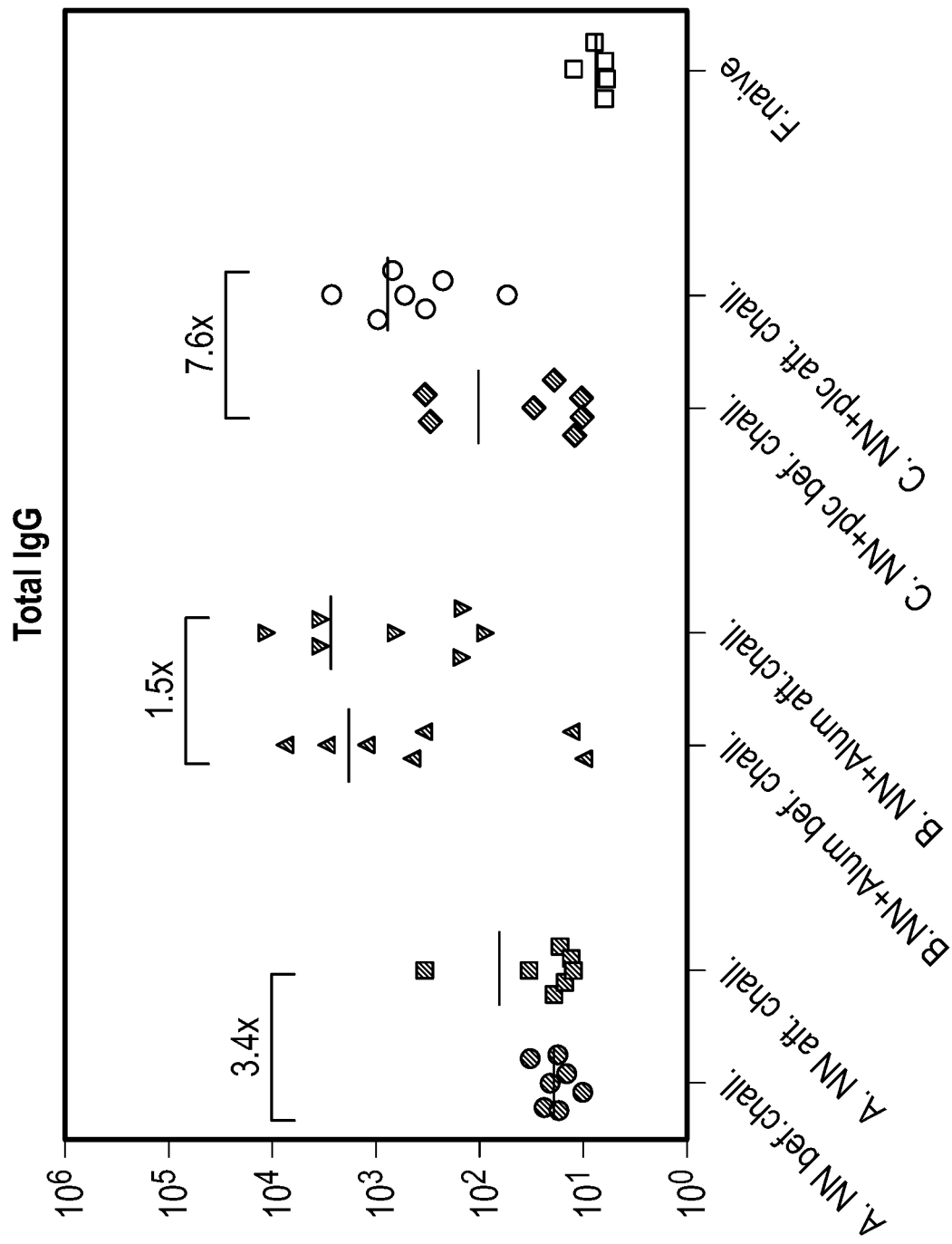
FIG. 4 shows that alum is a better adjuvant than PolyIC for the immunogenic fusion proteins according to the present invention.

The results are shown in FIG. 4. The mice were immunized with 3 μg of the RibN-AlpC-N (referred to as GBS-NN) fusion protein of WO 2008127179.

Accordingly, in a preferred embodiment of the vaccine according to the third aspect of the present invention the vaccine further comprises aluminium hydroxide as an adjuvant.

Further, in one embodiment of the vaccine according to the third aspect of the present invention the vaccine consists of a pharmaceutically effective vehicle, aluminium hydroxide, and the immunogenic product of according to the second aspect of the present invention, wherein, in the immunogenic product according to the second aspect of the present invention, the immunogenic fusion protein consists of the amino acid sequence shown in SEQ ID NO:12 and the second immunogenic fusion protein consists of the amino acid sequence shown in SEQ ID NO 6. Preferably there are no other proteins or amino acids sequences, different from the amino acid sequences in SEQ ID NO:6 and 12, in the vaccine.

In a further embodiment of the third aspect of the present invention the vaccine, alternatively or further, comprises a host cell according to the seventh aspect of the present invention In a further embodiment of the third aspect of the present invention the immunogenic fusion protein is conjugated to a capsular polysaccharide, preferably a bacterial polysaccharide, more preferably a group B *Streptococcus* polysaccharide. The use of a polypeptide, protein or fusion protein as a carrier for a polysaccharide in a conjugate vaccine is well known in the art, see for example U.S. Pat. No. 6,855,321, WO 9410317 and U.S. Pat. No. 4,496,538).

By polysaccharide is meant any linear or branched polymer consisting of monosaccharide residues, usually linked by glycosidic linkages, and thus includes oligosaccharides. Preferably, the polysaccharide will contain between 2 and 50 monosaccharide unites, more preferably between 6 and 30 monosaccharide units. The polysaccharide component may be based on or derived from polysaccharide components of the polysaccharide capsule from many Gram positive and Gram negative bacterial pathogens such as *H. influenzae, N. meningitidis* and *S. pneumoniae*. Other bacteria from which polysaccharide components may be conjugated to the carrier proteins of the present invention include *Staphylococcus aureus, Klebsiella, Pseudomonas, Salmonella typhi, Pseudomonas aeruginosa*, and *Shigella dysenteriae*. Polysaccharide components suitable for use according to this aspect of the present invention include the Hib oligosaccharide, lipopolysaccharide from *Pseudomonas aeruginosa* (Seid and Sadoff, 1981), lipopolysaccharides from *Salmonella* (Konadu et al., 1996) and the O-specific polysaccharide from *Shigella dysenteriae* (Chu et al, 1991). Other polysaccharide components suitable for use in accordance with the present invention will be well-known to those skilled in the art. Fragments of bacterial capsular polysaccharide may be produced by any suitable method, such as by acid hydrolysis or ultrasonic irradiation (Szn et al, 1986). Other methods of preparation of the polysaccharide components will be well known to those of skill in the art.

In one embodiment of the present invention, the polysaccharide is a capsular polysaccharide derived from group B *Streptococcus*, or their equivalents.

The polysaccharide component of the conjugate vaccine should preferably be coupled to the carrier protein by a covalent linkage. A particularly preferred method of coupling polysaccharide and protein is by reductive amination. Other methods include: activation of the polysaccharide with cyanogen bromide followed by reaction with adipic acid dihydrazide (spacer) and by conjugation to carboxide groups of carrier protein using soluble carbodiimides (Shneerson et al, 1986); functionalisation of the carrier protein with adipic acid dihydrazide followed by coupling to cyanogen bromide activated polysaccharides (Dick et al, 1989); chemical modification of both the carrier protein and the polysaccharide followed by their coupling (Marburg et at, 1986; Marburg et al, 1987 and 1989).

The polysaccharide molecule may be coupled to the carrier protein by a spacer molecule, such as adipic acid. This spacer molecule can be used to facilitate the coupling of protein to polysaccharide. After the coupling reaction has been performed, the conjugate may be purified by diafiltration or other known methods to remove unreacted protein or polysaccharide components.

If the polysaccharide is derived from a bacterial pathogen different from GBS, the conjugate may elicit immunity against two or more pathogens, e.g. multiple types of bacteria. This is a potentially important application of the immunogenic fusion protein. For the preparation of a conjugate vaccine, it would be a considerable advantage that the protein part is composed of a single fusion protein.

It is apparent to an artisan of skill in the art that vaccine composition of the present invention may comprise other substances or compounds not mentioned above, such as other diluents, emulsifying or stabilizing agents, or other proteins or polysaccharides. Such substances or compounds should confer desired properties to the composition.

The vaccine according to the third aspect of the present invention may be administrated parenterally, intramuscularly, intravenously, intraperitoneally, intradermally, mucosally, submucosally, topically or subcutaneously.

A fourth aspect of the present invention concerns the vaccine according to the third aspect of the present invention for use in preventing or treating an infection caused by a group B *Streptococcus*.

A fifth aspect of the present invention concerns a nucleotide sequence comprising
- at least one first nucleotide sequence as shown in SEQ ID NO:7 or fragments thereof fused, for example by being connected chemically, by being conjugated, or by being cross-linked, to
- at least one second nucleotide sequence as shown in SEQ ID NO:9 or fragments thereof, or alternatively,
- at least one nucleotide sequence as shown in SEQ ID NO:11.

A sixth aspect of the present invention concerns a vector comprising the nucleotide sequence according to the fifth aspect of the present invention.

A wide variety of expression host/vector combinations may be employed in expressing the nucleotide sequences of this invention. Useful expression vectors for eukaryotic hosts include, for example, vectors comprising expression control sequences from SV40, bovine papilloma virus, adenovirus, adeno-associated virus, cytomegalovirus, and retroviruses. Useful expression vectors for bacterial hosts include bacterial plasmids, such as those from *E. coli*, including pBluescript, pGEX2T, pUC vectors, col E1, pCR1, pBR322, pMB9 and their derivatives, wider host range plasmids, such as RP4, phage DNAs, e.g., the numerous derivatives of phage lambda, e.g., lambda GT10 and lambda GT11, NM989, and other DNA phages, such as M13 and filamentous single stranded DNA phages. Useful expression vectors for yeast cells include the 2.mu. plasmid and derivatives thereof. Useful vectors for insect cells include pVL 941.

In addition, any of a wide variety of expression control sequences may be used in these vectors to express the nucleotide sequences/DNA sequences of this invention. Useful expression control sequences include the expression control sequences associated with structural genes of the foregoing expression vectors. Examples of useful expression control sequences include, for example, the early and late promoters of SV40 or adenovirus, the lac system, the trp system, the TAC or TRC system, the T3 and T7 promoters, the major operator and promoter regions of phage lambda, the control regions of fd coat protein, the promoter for 3-phosphoglycerate kinase or other glycolytic enzymes, the promoters of acid phosphatase, e.g., Pho5, the promoters of the yeast alpha-mating system and other constitutive and inducible promoter sequences known to control the expression of genes of prokaryotic or eukaryotic cells or their viruses, and various combinations thereof.

A seventh aspect of the present invention concerns a host cell comprising the vector according to the sixth aspect of the present invention.

In one embodiment of the seventh aspect of the present invention the host cell may be a gram negative bacterial cell, gram positive bacterial cell, yeast cell, insect cell, animal cell, African green monkey cell, human cell, or plant cell.

In further embodiments of the host cell according to the seventh aspect of the present invention the host cell may be selected from the group consisting of *E. coli, Pseudomonas, Bacillus, Streptomyces, aspergillus, lactobacillus, shigella, salmonella, listeria, streptococcus, staphylococcus* and fungi. *E. coli* is however preferred.

A wide variety of unicellular host cells are useful in expressing the nucleotide sequences/DNA sequences of this invention. These hosts may include well known eukaryotic and prokaryotic hosts, such as both gram negative and gram positive strains, such as strains of *E. coli, Pseudomonas, Bacillus, Streptomyces, streptococcus, staphylococcus, lactobacillus, aspergillus, shigella, salmonella, listeria*, fungi, yeast, insect cells such as *Spodoptera frugiperda* (SF9), animal cells such as CHO and mouse cells, African green monkey cells such as COS 1, COS 7, BSC 1, BSC 40, and BMT 10, human cells, and plant cells in tissue culture. Preferred host organisms include bacteria such as *E. coli* and *B. subtilis*, and mammalian cells in tissue culture.

It should, of course, be understood that not all vectors and expression control sequences will function equally well to express the nucleotide sequences/DNA sequences of this invention. Neither will all hosts function equally well with the same expression system. However, one of skill in the art may make a selection among these vectors, expression control sequences and hosts without undue experimentation and without departing from the scope of this invention. For example, in selecting a vector, the host must be considered because the vector must replicate in it. The vector's copy number, the ability to control that copy number, and the expression of any other proteins encoded by the vector, such as antibiotic markers, should also be considered. In selecting an expression control sequence, a variety of factors should also be considered. These include, for example, the relative strength of the sequence, its controllability, and its compatibility with the nucleotide sequences/DNA sequences of this invention, particularly as regards potential secondary structures. Unicellular hosts should be selected by consideration of their compatibility with the chosen vector, the toxicity of the product coded for by the nucleotide sequences/DNA sequences of this invention, their secretion characteristics, their ability to fold the protein correctly, their fermentation or culture requirements, and the ease of purification from them of the products coded for by the nucleotide sequences/ DNA sequences of this invention. Within these parameters, one of skill in the art may select various vector/expression control sequence/host combinations that will express the nucleotide sequences/DNA sequences of this invention on cultivation or in large-scale animal culture.

The polypeptides, i.e. the N-terminal fragments, proteins and immunogenic fusion protein, encoded by the nucleotide sequences/DNA sequences of this invention may be isolated from the microbial culture or cell culture and purified using any of a variety of conventional methods including: liquid chromatography such as normal or reversed phase, using HPLC, FPLC and the like; affinity chromatography (such as with inorganic ligands or monoclonal antibodies); ion exchange chromatography, size exclusion chromatography; immobilized metal chelate chromatography; gel electrophoresis; tangential flow filtration and the like. One of skill in the art may select the most appropriate isolation and purification techniques without departing from the scope of this invention.

In addition, the polypeptides, i.e. the N-terminal fragments, proteins and immunogenic fusion protein of this invention may be generated by any of several chemical techniques. For example, they may be prepared using the solid-phase synthetic technique originally described by R. B. Merrifield (J Am Chem Soc 1963 83:2149-54), or they may be prepared by synthesis in solution. A summary of peptide synthesis techniques may be found in E. Gross & H. J. Meinhofer, 4 The Peptides: Analysis Synthesis, Biology; Modern Techniques Of Peptide And Amino Acid Analysis, John Wiley & Sons, (1981); and M. Bodanszky, Principles Of Peptide Synthesis, Springer-Verlag (1984).

An eight aspect of the present invention concerns a method of producing an immunogenic fusion protein comprising the steps of
  a. Providing a host cell according to the seventh aspect of the present invention,
  b. Multiplying the host cell,
  c. Purifying the immunogenic fusion protein according to the first aspect of the present invention and
  d. Obtaining the immunogenic fusion protein.

Alternatively the immunogenic fusion protein can be produced in a cell-free expression system.

Such systems comprise all essential factors for expression from an appropriate recombinant nucleic acid, operably linked to a promoter that will function in that particular system.

A ninth aspect of the present invention concerns a method for preventing or treating an infection caused by a group B *Streptococcus* which comprises administering to an individual an effective amount of a vaccine as described herein.

These methods comprise administering to an individual a pharmaceutically effective amount of the vaccine of the invention. There is also, according to the present invention, provided a use of the immunogenic composition of the invention for the manufacture of a vaccine for preventing or treating an infection caused by a group B *Streptococcus*.

Maternal immunoprophylaxis with a vaccine, for protecting against infection to group B *Streptococcus* both in the mother and in the young infant, has long been proposed as a potential route.

Thus one embodiment of the method according to the ninth aspect of the present invention comprises administering to a human female an effective amount of a vaccine as described herein capable of conferring immunity to the infection to an unborn offspring of the human female.

According to this embodiment, the vaccine is administered to a non-pregnant female or to a pregnant female, under conditions of time and amount sufficient to cause the production of antibodies which serve to protect both the female and a fetus or newborn (via passive transfer of antibodies across the placenta).

The terms "preventing or treating" in its various grammatical forms in relation to the present invention refer to preventing, curing, reversing, attenuating, alleviating, ameliorating, inhibiting, minimizing, suppressing, or halting (1) the deleterious effects of a disorder associated with group B *Streptococcus* infection, (2) disorder progression, or (3) disorder causative agent (group B *Streptococcus*). Further, the terms "preventing or treating" are contemplated to include the creation of total or partial immunity of the individual to group B *Streptococcus* infection.

A tenth aspect of the present invention concerns a method for preventing or treating an infection caused by a group B *Streptococcus* which comprises administering to an individual in need thereof an effective amount of antibodies elicited from the exposure of a second individual to a vaccine according to one aspect of the invention.

According to this embodiment, resistance to group B *Streptococcus* is conferred to the individual by passive immunization, i.e., the vaccine is provided to a host (i.e. a human or mammal) volunteer, and the elicited antisera is recovered and directly provided to a recipient suspected of having an infection caused by a group B *Streptococcus*. It is contemplated that such antisera could be administered to a pregnant female (at or prior to parturition), under conditions of time and amount sufficient so that the antisera would serve to protect either the fetus or newborn (via passive incorporation of the antibodies across the placenta).

The vaccine or antisera of the present invention may, thus, be provided either prior to the onset of infection (so as to prevent or attenuate an anticipated infection) or after the initiation of an actual infection.

The vaccine may be administered to humans or animals, including mammals and birds, such as rodents (mouse, rat, guinea pig, or rabbit); birds (turkey, hen or chicken); other farm animals (cow, horse, pig or piglet); pets (dog, cat and other pets); and humans. While many animals may be treated with the vaccine of the invention, a preferred individual for treatment is a human or commercially valuable animal and livestock such as fish, e.g. Tilapia, and camels.

The vaccine can be administered to an individual according to methods known in the art. Such methods comprise application e.g. parenterally, such as through all routes of injection into or through the skin: e.g. intramuscular, intravenous, intraperitoneal, intradermal, mucosal, submucosal, or subcutaneous. Also, they may be applied by topical application as a drop, spray, gel or ointment to the mucosal epithelium of the eye, nose, mouth, anus, or vagina, or onto the epidermis of the outer skin at any part of the body. Other possible routes of application are by spray, aerosol, or powder application through inhalation via the respiratory tract. In this last case the particle size that is used will determine how deep the particles will penetrate into the respiratory tract. Alternatively, application can be via the alimentary route, by combining with the food, feed or drinking water e.g. as a powder, a liquid, or tablet, or by administration directly into the mouth as a: liquid, a gel, a tablet, or a capsule, or to the anus as a suppository. The vaccine may also be administrated in the form of a DNA vaccine.

Many different techniques exist for the timing of the immunizations. It is possible to use the compositions of the invention more than once to increase the levels and diversities of expression of the immunoglobulin repertoire expressed by the immunized animal. Typically, if multiple immunizations are given, they will be given one to two months apart.

The term "effective amount" in relation to the present invention refers to that amount which provides a therapeutic effect for a given condition and administration regimen. This is a predetermined quantity of active material calculated to produce a desired therapeutic effect in association with the required additives and diluents; i.e., a carrier, or administration vehicle. Further, it is intended to mean an amount sufficient to reduce and most preferably prevent a clinically significant deficit in the activity and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluents; i.e., carrier, or additive. Further, the dosage to be administered will vary depending on the active principle or principles to be used, the age, weight etc of the individual to be treated.

Dose-finding experiments have been done for the previously described fusion protein disclosed in WO 2008127179 in both mice and humans. In mice dose-response was seen at doses from approximately 80 ng to 2 μg in the presence of Alhydrogel, i.e. AlOH, with a plateau reached above 2 μg. In humans, 10 ug, 50 μg and 100 μg doses were tested in the absence or presence of Alhydrogel. For the alhydrogel group, the 10 μg dose was just at the top of the dose response curve, and 50 and 250 μg at the plateau. The preferred human doses of the immunogenic fusion protein according to the first aspect of the present invention in the presence of Alhydrogel is therefore within the range of 1 to 250 μg, preferably 10 to 150 μg, preferably 25 to 100 μg or 40 to 80 μg. In the absence of Alhydrogel, the preferred human doses of the immunogenic fusion protein according to the first aspect of the present invention would be 10 to 100 μg, preferably 50 to 500 μg, or preferably 100 to 250 μg.

Generally, the dosage may consist of an initial injection, most probably with adjuvant, followed most probably by one or maybe more booster injections. Preferably, booster injections may be administered at about 1 and 6 months after the initial injection.

The invention claimed is:

1. An immunogenic fusion protein consisting of an amino acid sequence having at least 90% sequence identity with the amino acid sequence shown in SEQ ID NO:12.

2. The immunogenic fusion protein according to claim 1, wherein the amino acid sequence has at least 95% sequence identity with the amino acid sequence shown in SEQ ID NO:12.

3. The immunogenic fusion protein according to claim 1, wherein the amino acid sequence has at least 99% sequence identity with the amino acid sequence shown in SEQ ID NO:12.

4. The immunogenic fusion protein according to claim 1, wherein the amino acid sequence consists of the amino acid sequence shown in SEQ ID NO:12.

5. An immunogenic composition comprising the immunogenic fusion protein according to claim 1 and a pharmaceutically acceptable vehicle.

6. The immunogenic composition according to claim 5, further comprising aluminium hydroxide.

* * * * *

SEQUENCE LISTING

```
<160> NUMBER OF SEQ ID NOS: 14

<210> SEQ ID NO 1
<211> LENGTH: 537
<212> TYPE: DNA
<213> ORGANISM: Streptococcus sp.

<400> SEQUENCE: 1
gggcccctgg gatccgctga agtaatttca ggaagtgctg ttacgttaaa cacaaatatg      60
```

```
actaaaaatg ttcagaatgg tagagcatat atagatttat atgatgtgaa aaatgggaaa      120
atagatccat tacaattaat tacgttaaat tcacctgatt taaaagctca gtatgtcatt      180
aggcaaggcg gcaattattt cacacaacct tctgaattga ctactgttgg tgcagctagt      240
attaattata cagtattgaa gacagatgga agtcctcata cgaagcctga tggacaagtg      300
gatattataa acgtttcatt gactatttac aattcttcag ctttgagaga taaaatagat      360
gaagttaaaa agaaagcgga agaccctaaa tgggacgagg gaagtcgcga taaagttttg      420
ataagtttag atgatatcaa aacagatatt gataataatc ctaagacgca atcagacatt      480
gccaataaaa taactgaagt tactaattta gaaaaaatac tagtacctcg aatccca        537
```

<210> SEQ ID NO 2
<211> LENGTH: 179
<212> TYPE: PRT
<213> ORGANISM: Streptococcus sp.

<400> SEQUENCE: 2

```
Gly Pro Leu Gly Ser Ala Glu Val Ile Ser Gly Ser Ala Val Thr Leu
1               5                   10                  15

Asn Thr Asn Met Thr Lys Asn Val Gln Asn Gly Arg Ala Tyr Ile Asp
            20                  25                  30

Leu Tyr Asp Val Lys Asn Gly Lys Ile Asp Pro Leu Gln Leu Ile Thr
        35                  40                  45

Leu Asn Ser Pro Asp Leu Lys Ala Gln Tyr Val Ile Arg Gln Gly Gly
    50                  55                  60

Asn Tyr Phe Thr Gln Pro Ser Glu Leu Thr Thr Val Gly Ala Ala Ser
65                  70                  75                  80

Ile Asn Tyr Thr Val Leu Lys Thr Asp Gly Ser Pro His Thr Lys Pro
                85                  90                  95

Asp Gly Gln Val Asp Ile Ile Asn Val Ser Leu Thr Ile Tyr Asn Ser
            100                 105                 110

Ser Ala Leu Arg Asp Lys Ile Asp Glu Val Lys Lys Ala Glu Asp
        115                 120                 125

Pro Lys Trp Asp Glu Gly Ser Arg Asp Lys Val Leu Ile Ser Leu Asp
    130                 135                 140

Asp Ile Lys Thr Asp Ile Asp Asn Asn Pro Lys Thr Gln Ser Asp Ile
145                 150                 155                 160

Ala Asn Lys Ile Thr Glu Val Thr Asn Leu Glu Lys Ile Leu Val Pro
                165                 170                 175

Arg Ile Pro
```

<210> SEQ ID NO 3
<211> LENGTH: 525
<212> TYPE: DNA
<213> ORGANISM: Streptococcus sp.

<400> SEQUENCE: 3

```
gggcccctgg gatcctctac aattccaggg agtgcagcga ccttaaatac aagcatcact      60
aaaaatatac aaaacggaaa tgcttacata gattatatg atgtaaaatt aggtaaaata      120
gatccattac aattaattgt tttagaacaa ggttttacag caaagtatgt ttttagacaa      180
ggtactaaat actatgggga tgtttctcag ttgcagagta caggaagggc tagtcttacc      240
tataatatat ttggtgaaga tggactacca catgtaaaga ctgatggaca aattgatata      300
gttagtgttg ctttaactat ttatgattca acaaccttga gggataagat tgaagaagtt      360
```

| | |
|---|---:|
| agaacgaatg caaacgatcc taagtggacg gaagaaagtc gtactgaggt tttaacagga | 420 |
| ttagatacaa ttaagacaga tattgataat aatcctaaga cgcaaacaga tattgatagt | 480 |
| aaaattgttg aggttaatga attagagaaa ttgttagtat tgtca | 525 |

<210> SEQ ID NO 4
<211> LENGTH: 175
<212> TYPE: PRT
<213> ORGANISM: Streptococcus sp.

<400> SEQUENCE: 4

```
Gly Pro Leu Gly Ser Ser Thr Ile Pro Gly Ser Ala Ala Thr Leu Asn
1               5                   10                  15

Thr Ser Ile Thr Lys Asn Ile Gln Asn Gly Asn Ala Tyr Ile Asp Leu
            20                  25                  30

Tyr Asp Val Lys Leu Gly Lys Ile Asp Pro Leu Gln Leu Ile Val Leu
        35                  40                  45

Glu Gln Gly Phe Thr Ala Lys Tyr Val Phe Arg Gln Gly Thr Lys Tyr
    50                  55                  60

Tyr Gly Asp Val Ser Gln Leu Gln Ser Thr Gly Arg Ala Ser Leu Thr
65                  70                  75                  80

Tyr Asn Ile Phe Gly Glu Asp Gly Leu Pro His Val Lys Thr Asp Gly
                85                  90                  95

Gln Ile Asp Ile Val Ser Val Ala Leu Thr Ile Tyr Asp Ser Thr Thr
            100                 105                 110

Leu Arg Asp Lys Ile Glu Glu Val Arg Thr Asn Ala Asn Asp Pro Lys
        115                 120                 125

Trp Thr Glu Glu Ser Arg Thr Glu Val Leu Thr Gly Leu Asp Thr Ile
    130                 135                 140

Lys Thr Asp Ile Asp Asn Asn Pro Lys Thr Gln Thr Asp Ile Asp Ser
145                 150                 155                 160

Lys Ile Val Glu Val Asn Glu Leu Glu Lys Leu Leu Val Leu Ser
                165                 170                 175
```

<210> SEQ ID NO 5
<211> LENGTH: 1053
<212> TYPE: DNA
<213> ORGANISM: Streptococcus sp.

<400> SEQUENCE: 5

| | |
|---|---:|
| gggcccctgg gatccgctga agtaatttca ggaagtgctg ttacgttaaa cacaaatatg | 60 |
| actaaaaatg ttcagaatgg tagagcatat atagatttat atgatgtgaa aaatgggaaa | 120 |
| atagatccat acaattaat tacgttaaat tcacctgatt taaaagctca gtatgtcatt | 180 |
| aggcaaggcg gcaattattt cacacaacct tctgaattga ctactgttgg tgcagctagt | 240 |
| attaattata cagtattgaa gacagatgga agtcctcata cgaagcctga tggacaagtg | 300 |
| gatattataa acgtttcatt gactatttac aattcttcag ctttgagaga taaaatagat | 360 |
| gaagttaaaa agaaagcgga agaccctaaa tgggacgagg aagtcgcgta taagttttg | 420 |
| ataagtttag atgatatcaa aacagatatt gataataatc ctaagacgca atcagacatt | 480 |
| gccaataaaa taactgaagt tactaattta gaaaaaatac tagtacctcg aatcccagaa | 540 |
| ttctctacaa ttccagggag tgcagcgacc ttaaatacaa gcatcactaa aaatatacaa | 600 |
| aacggaaatg cttacataga tttatatgat gtaaaattag gtaaaataga tccattacaa | 660 |
| ttaattgttt tagaacaagg ttttacagca aagtatgttt ttagacaagg tactaaatac | 720 |

```
tatggggatg tttctcagtt gcagagtaca ggaagggcta gtcttaccta taatatattt    780
ggtgaagatg gactaccaca tgtaaagact gatggacaaa ttgatatagt tagtgttgct    840
ttaactattt atgattcaac aaccttgagg gataagattg aagaagttag aacgaatgca    900
aacgatccta agtggacgga agaaagtcgt actgaggttt taacaggatt agatacaatt    960
aagacagata ttgataataa tcctaagacg caaacagata ttgatagtaa aattgttgag    1020
gttaatgaat tagagaaatt gttagtattg tca                                 1053

<210> SEQ ID NO 6
<211> LENGTH: 378
<212> TYPE: PRT
<213> ORGANISM: Streptococcus sp.

<400> SEQUENCE: 6

Gly Pro Leu Gly Ser Ala Ser Val Leu Ile Gly Ile Ser Phe Leu Gly
1               5                   10                  15

Gly Phe Thr Gln Gly Gln Phe Asn Ile Ser Thr Asp Thr Val Phe Ala
            20                  25                  30

Ala Glu Val Ile Ser Gly Ser Ala Val Thr Leu Asn Thr Asn Met Thr
        35                  40                  45

Lys Asn Val Gln Asn Gly Arg Ala Tyr Ile Asp Leu Tyr Asp Val Lys
    50                  55                  60

Asn Gly Lys Ile Asp Pro Leu Gln Leu Ile Thr Leu Asn Ser Pro Asp
65                  70                  75                  80

Leu Lys Ala Gln Tyr Val Ile Arg Gln Gly Gly Asn Tyr Phe Thr Gln
                85                  90                  95

Pro Ser Glu Leu Thr Thr Val Gly Ala Ala Ser Ile Asn Tyr Thr Val
            100                 105                 110

Leu Lys Thr Asp Gly Ser Pro His Thr Lys Pro Asp Gly Gln Val Asp
        115                 120                 125

Ile Ile Asn Val Ser Leu Thr Ile Tyr Asn Ser Ser Ala Leu Arg Asp
    130                 135                 140

Lys Ile Asp Glu Val Lys Lys Lys Ala Glu Asp Pro Lys Trp Asp Glu
145                 150                 155                 160

Gly Ser Arg Asp Lys Val Leu Ile Ser Leu Asp Asp Ile Lys Thr Asp
                165                 170                 175

Ile Asp Asn Asn Pro Lys Thr Gln Ser Asp Ile Ala Asn Lys Ile Thr
            180                 185                 190

Glu Val Thr Asn Leu Glu Lys Ile Leu Val Pro Arg Ile Pro Glu Phe
        195                 200                 205

Ser Thr Ile Pro Gly Ser Ala Ala Thr Leu Asn Thr Ser Ile Thr Lys
    210                 215                 220

Asn Ile Gln Asn Gly Asn Ala Tyr Ile Asp Leu Tyr Asp Val Lys Leu
225                 230                 235                 240

Gly Lys Ile Asp Pro Leu Gln Leu Ile Val Leu Glu Gln Gly Phe Thr
                245                 250                 255

Ala Lys Tyr Val Phe Arg Gln Gly Thr Lys Tyr Tyr Gly Asp Val Ser
            260                 265                 270

Gln Leu Gln Ser Thr Gly Arg Ala Ser Leu Thr Tyr Asn Ile Phe Gly
        275                 280                 285

Glu Asp Gly Leu Pro His Val Lys Thr Asp Gly Gln Ile Asp Ile Val
    290                 295                 300

Ser Val Ala Leu Thr Ile Tyr Asp Ser Thr Thr Leu Arg Asp Lys Ile
```

```
                305                 310                 315                 320
Glu Glu Val Arg Thr Asn Ala Asn Asp Pro Lys Trp Thr Glu Ser
            325                 330                 335

Arg Thr Glu Val Leu Thr Gly Leu Asp Thr Ile Lys Thr Asp Ile Asp
            340                 345                 350

Asn Asn Pro Lys Thr Gln Thr Asp Ile Asp Ser Lys Ile Val Glu Val
            355                 360                 365

Asn Glu Leu Glu Lys Leu Leu Val Leu Ser
            370                 375

<210> SEQ ID NO 7
<211> LENGTH: 525
<212> TYPE: DNA
<213> ORGANISM: Streptococcus sp.

<400> SEQUENCE: 7
atggccgaag ttattagcgg tagcgcagca accctgaata gcgcactggt taaaaatgtt     60
agcggtggca aagcctatat cgacatctat gatgtgaaaa acggcaaaat tgatccgctg    120
aatctgattg ttctgcctcc gagcaattat agcgccaact attatatcaa acagggtggt    180 cgcatttttca ccaatgttaa tcagctgcag acaccgggta cagcaaccat tacctataac    240
attctggatg aaaatggcaa cccgtatacc aaaagtgatg gccagattga tattgttagc    300
ctggttacca ccgtttatga taccaccgaa ctgcgcaata acatcaacaa agttattgag    360
aatgccaacg acccgaaatg gtcagatgat agccgtaaag atgttctgag caaaatcgag    420
gtgatcaaaa acgatattga taacaacccg aaaacccaga gcgatatcga caacaaaatt    480
gtggaagtga acgagctgga aaaactgctg gttctgccgt aataa                    525

<210> SEQ ID NO 8
<211> LENGTH: 173
<212> TYPE: PRT
<213> ORGANISM: Streptococcus sp.

<400> SEQUENCE: 8

Met Ala Glu Val Ile Ser Gly Ser Ala Ala Thr Leu Asn Ser Ala Leu
1               5                   10                  15

Val Lys Asn Val Ser Gly Gly Lys Ala Tyr Ile Asp Ile Tyr Asp Val
            20                  25                  30

Lys Asn Gly Lys Ile Asp Pro Leu Asn Leu Ile Val Leu Thr Pro Ser
        35                  40                  45

Asn Tyr Ser Ala Asn Tyr Tyr Ile Lys Gln Gly Gly Arg Ile Phe Thr
    50                  55                  60

Ser Val Asn Gln Leu Gln Thr Pro Gly Thr Ala Thr Ile Thr Tyr Asn
65                  70                  75                  80

Ile Leu Asp Glu Asn Gly Asn Pro Tyr Thr Lys Ser Asp Gly Gln Ile
                85                  90                  95

Asp Ile Val Ser Leu Val Thr Thr Val Tyr Asp Thr Thr Glu Leu Arg
            100                 105                 110

Asn Asn Ile Asn Lys Val Ile Glu Asn Ala Asn Asp Pro Lys Trp Ser
        115                 120                 125

Asp Asp Ser Arg Lys Asp Val Leu Ser Lys Ile Glu Val Ile Lys Asn
    130                 135                 140

Asp Ile Asp Asn Asn Pro Lys Thr Gln Ser Asp Ile Asp Asn Lys Ile
145                 150                 155                 160

Val Glu Val Asn Glu Leu Glu Lys Leu Leu Val Leu Pro
                165                 170
```

165 170

<210> SEQ ID NO 9
<211> LENGTH: 528
<212> TYPE: DNA
<213> ORGANISM: Streptococcus sp.

<400> SEQUENCE: 9

| | | | | | |
|---|---|---|---|---|---|
| atggcaagca | ccattccggg | tagcgcagca | accctgaata | ccagcattac | caaaaacatt | 60 |
| cagaatggca | acgcctatat | cgatctgtat | gatgtgaaaa | acggtctgat | tgatccgcag | 120 |
| aatctgattg | ttctgaatcc | gagcagctat | agcgccaact | attatatcaa | acagggtgcc | 180 |
| aaatattaca | gcaacccgag | cgaaattacc | accaccggta | gcgcaaccat | tacctttaac | 240 |
| attctggatg | aaaccggcaa | cccgcataaa | aaagcagatg | gtcagattga | tattgtgagc | 300 |
| gttaacctga | ccatttatga | tagcaccgca | ctgcgtaatc | gtattgatga | agttattaac | 360 |
| aatgccaacg | acccgaaatg | gtctgatggt | agccgtgatg | aagtgctgac | cggtctggaa | 420 |
| aaaatcaaaa | aagatatcga | taacaacccg | aaaacccaga | tcgacattga | caacaaaatt | 480 |
| aacgaagtga | acgaaatcga | aaaactgctg | gttgttagcc | tgtaataa | | 528 |

<210> SEQ ID NO 10
<211> LENGTH: 173
<212> TYPE: PRT
<213> ORGANISM: Streptococcus sp.

<400> SEQUENCE: 10

Ala Ser Thr Ile Pro Gly Ser Ala Ala Thr Leu Asn Thr Ser Ile Thr
1               5                   10                  15

Lys Asn Ile Gln Asn Gly Asn Ala Tyr Ile Asp Leu Tyr Asp Val Lys
            20                  25                  30

Asn Gly Leu Ile Asp Pro Gln Asn Leu Ile Val Leu Asn Pro Ser Ser
        35                  40                  45

Tyr Ser Ala Asn Tyr Tyr Ile Lys Gln Gly Ala Lys Tyr Tyr Ser Asn
    50                  55                  60

Pro Ser Glu Ile Thr Thr Thr Gly Ser Ala Thr Ile Thr Phe Asn Ile
65                  70                  75                  80

Leu Asp Glu Thr Gly Asn Pro His Lys Lys Ala Asp Gly Gln Ile Asp
                85                  90                  95

Ile Val Ser Val Asn Leu Thr Ile Tyr Asp Ser Thr Ala Leu Arg Asn
            100                 105                 110

Arg Ile Asp Glu Val Ile Asn Asn Ala Asn Asp Pro Lys Trp Ser Asp
        115                 120                 125

Gly Ser Arg Asp Glu Val Leu Thr Gly Leu Glu Lys Ile Lys Lys Asp
    130                 135                 140

Ile Asp Asn Asn Pro Lys Thr Gln Ile Asp Ile Asp Asn Lys Ile Asn
145                 150                 155                 160

Glu Val Asn Glu Ile Glu Lys Leu Leu Val Val Ser Leu
                165                 170

<210> SEQ ID NO 11
<211> LENGTH: 1047
<212> TYPE: DNA
<213> ORGANISM: Streptococcus sp.

<400> SEQUENCE: 11
atggccgaag ttattagcgg tagcgcagca accctgaata gcgcactggt taaaaatgtt   60

```
agcggtggca aagcctatat cgacatctat gatgtgaaaa acggcaaaat tgatccgctg    120
aatctgattg ttctgcctcc gagcaattat agcgccaact attatatcaa acagggtggt    180
cgcattttca ccaatgttaa tcagctgcag acaccgggta cagcaaccat tacctataac    240
attctggatg aaaatggcaa cccgtatacc aaaagtgatg ccagattga tattgttagc     300 ctggttacca ccgtttatga taccaccgaa ctgcgcaata acatcaacaa agttattgag    360
aatgccaacg acccgaaatg gtcagatgat agccgtaaag atgttctgag caaaatcgag    420
gtgatcaaaa acgatattga taacaacccg aaacccaga gcgatatcga acaacaaatt     480
gtggaagtga acgagctgga aaaactgctg gttctgccgg aatttagcac cattccgggt    540
tcagcagcca cactgaatac cagcattacc aaaaacattc agaatggcaa cgcctacatt    600
gatctgtacg atgtaaaaaa tggtctgatc gatccgcaga acctgatcgt gctgaatccg    660
agcagctatt cagccaatta ttatattaaa caaggcgcaa atactatag caacccgagc     720 gaaattacca ccaccggtag cgccaccatt acgtttaata tcctggacga accggtaac    780 ccgcataaaa aagcagatgg tcaaattgat atcgtgagcg ttaacctgac gatttatgat    840
agcacagccc tgcgtaatcg tattgatgaa gtgattaata cgcgaatga tcctaaatgg    900 tccgatggta gtcgtgatga agtactgacc ggtctgaaaa aatcaaaaa agacatcgac    960 aataatccga aaacgcagat tgacattgac aataaaatca cgaggtgaa cgagatcgag   1020 aaactgctgg tagttagcct gtaataa                                       1047

<210> SEQ ID NO 12
<211> LENGTH: 347
<212> TYPE: PRT
<213> ORGANISM: Streptococcus sp.

<400> SEQUENCE: 12

Met Ala Glu Val Ile Ser Gly Ser Ala Ala Thr Leu Asn Ser Ala Leu
1               5                   10                  15

Val Lys Asn Val Ser Gly Gly Lys Ala Tyr Ile Asp Ile Tyr Asp Val
            20                  25                  30

Lys Asn Gly Lys Ile Asp Pro Leu Asn Leu Ile Val Leu Thr Pro Ser
        35                  40                  45

Asn Tyr Ser Ala Asn Tyr Tyr Ile Lys Gln Gly Gly Arg Ile Phe Thr
    50                  55                  60

Ser Val Asn Gln Leu Gln Thr Pro Gly Thr Ala Thr Ile Thr Tyr Asn
65                  70                  75                  80

Ile Leu Asp Glu Asn Gly Asn Pro Tyr Thr Lys Ser Asp Gly Gln Ile
                85                  90                  95

Asp Ile Val Ser Leu Val Thr Thr Val Tyr Asp Thr Thr Glu Leu Arg
            100                 105                 110

Asn Asn Ile Asn Lys Val Ile Glu Asn Ala Asn Asp Pro Lys Trp Ser
        115                 120                 125

Asp Asp Ser Arg Lys Asp Val Leu Ser Lys Ile Glu Val Ile Lys Asn
    130                 135                 140

Asp Ile Asp Asn Asn Pro Lys Thr Gln Ser Asp Ile Asp Asn Lys Ile
145                 150                 155                 160

Val Glu Val Asn Glu Leu Glu Lys Leu Leu Val Leu Pro Glu Phe Ser
                165                 170                 175

Thr Ile Pro Gly Ser Ala Ala Thr Leu Asn Thr Ser Ile Thr Lys Asn
            180                 185                 190

Ile Gln Asn Gly Asn Ala Tyr Ile Asp Leu Tyr Asp Val Lys Asn Gly
```

```
                195                 200                 205
Leu Ile Asp Pro Gln Asn Leu Ile Val Leu Asn Pro Ser Ser Tyr Ser
    210                 215                 220

Ala Asn Tyr Tyr Ile Lys Gln Gly Ala Lys Tyr Tyr Ser Asn Pro Ser
225                 230                 235                 240

Glu Ile Thr Thr Thr Gly Ser Ala Thr Ile Thr Phe Asn Ile Leu Asp
                245                 250                 255

Glu Thr Gly Asn Pro His Lys Lys Ala Asp Gly Gln Ile Asp Ile Val
            260                 265                 270

Ser Val Asn Leu Thr Ile Tyr Asp Ser Thr Ala Leu Arg Asn Arg Ile
        275                 280                 285

Asp Glu Val Ile Asn Asn Ala Asn Asp Pro Lys Trp Ser Asp Gly Ser
    290                 295                 300

Arg Asp Glu Val Leu Thr Gly Leu Glu Lys Ile Lys Lys Asp Ile Asp
305                 310                 315                 320

Asn Asn Pro Lys Thr Gln Ile Asp Ile Asp Asn Lys Ile Asn Glu Val
                325                 330                 335

Asn Glu Ile Glu Lys Leu Leu Val Val Ser Leu
            340                 345
```

<210> SEQ ID NO 13
<211> LENGTH: 310
<212> TYPE: DNA
<213> ORGANISM: Streptococcus sp.

<400> SEQUENCE: 13

```
gtagttgaag gaagtgctgc aacattaaat actgccatga ctaaaaacat gcagaatggg      60
aatgcatata ttgatattta tgatgttaaa ttaggaaaaa ttgatccatt acaactgatt     120
aaattggaac cgggatacac tgctatttat tacattacac aaggttcaaa agtttatgca     180
aatgtttcgg agctacaaac accaggagca gcgaaagtta attatcgtat tcaaacctct     240
gatggaagcg atcatataaa atctgatggt caattagaca gcgttaatat ttcattaaca     300
gtttatgatt                                                            310
```

<210> SEQ ID NO 14
<211> LENGTH: 103
<212> TYPE: PRT
<213> ORGANISM: Streptococcus sp.

<400> SEQUENCE: 14

```
Val Val Glu Gly Ser Ala Ala Thr Leu Asn Thr Ala Met Thr Lys Asn
1               5                   10                  15

Met Gln Asn Gly Asn Ala Tyr Ile Asp Ile Tyr Asp Val Lys Leu Gly
            20                  25                  30

Lys Ile Asp Pro Leu Gln Leu Ile Lys Leu Glu Pro Gly Tyr Thr Ala
        35                  40                  45

Ile Tyr Tyr Ile Thr Gln Gly Ser Lys Val Tyr Ala Asn Val Ser Glu
    50                  55                  60

Leu Gln Thr Pro Gly Ala Ala Lys Val Asn Tyr Arg Ile Gln Thr Ser
65                  70                  75                  80

Asp Gly Ser Asp His Ile Lys Ser Asp Gly Gln Leu Asp Ser Val Asn
                85                  90                  95

Ile Ser Leu Thr Val Tyr Asp
            100
```